US006757621B2

(12) United States Patent
Mizuno et al.

(10) Patent No.: US 6,757,621 B2
(45) Date of Patent: *Jun. 29, 2004

(54) PROCESS MANAGEMENT SYSTEM

(75) Inventors: Fumio Mizuno, Tokorozawa (JP); Seiji Isogai, Hitachinaka (JP); Kenji Watanabe, Oume (JP); Yasuhiro Yoshitake, Yokosuka (JP); Terushige Asakawa, Hamura (JP); Yuichi Ohyama, Isezaki (JP); Hidekuni Sugimoto, Honjyo (JP); Seiji Ishikawa, Kawasaki (JP); Masataka Shiba, Yokohama (JP); Jun Nakazato, Shinagawa-ku (JP); Makoto Ariga, Yokohama (JP); Tetsuji Yokouchi, Yokohama (JP); Toshimitsu Hamada, Yokohama (JP); Ikuo Suzuki, Hitachinaka (JP); Masami Ikota, Higashiyamato (JP); Mari Nozoe, Oume (JP); Isao Miyazaki, Isezaki (JP); Yoshiharu Shigyo, Takasaki (JP)

(73) Assignees: Hitachi, Ltd., Tokyo (JP); Hitachi Engineering Co., Ltd., Hitachinaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/342,871
(22) Filed: Jan. 16, 2003
(65) Prior Publication Data
US 2003/0130806 A1 Jul. 10, 2003

Related U.S. Application Data

(63) Continuation of application No. 09/142,546, filed as application No. PCT/JP97/00898 on Mar. 19, 1997, now Pat. No. 6,542,830.

(30) Foreign Application Priority Data

Mar. 19, 1996 (JP) .............................................. 8-63012
Mar. 19, 1996 (JP) .............................................. 8-63013
Mar. 19, 1996 (JP) .............................................. 8-63014

(51) Int. Cl.$^7$ ............................................... H01L 21/66
(52) U.S. Cl. .............................. 702/35; 702/36; 702/40; 700/121
(58) Field of Search ............................... 702/33–36, 40, 702/81–84, 108, 117, 118, 120–122, 170, 172, 183–185, 188, 150, FOR 170, FOR 171, FOR 103, FOR 104, FOR 154, FOR 123–FOR 125, FOR 136, FOR 157, FOR 148, FOR 149; 700/108–110, 115–121; 438/14, 16–18; 250/370.01, 492.2; 382/145, 151

(56) References Cited

U.S. PATENT DOCUMENTS 5,483,636 A    1/1996   Saxena ................... 395/183.01

(List continued on next page.)

FOREIGN PATENT DOCUMENTS

EP          0 641 020         3/1995

(List continued on next page.)

OTHER PUBLICATIONS

*Automatic Parameter Warning System*, IBM Technical Disclosure Bulletin, US, IBM Corp., New York, vol. 35, No. 6, Nov. 1, 1992, p. 75–77.

* cited by examiner

Primary Examiner—Hal Wachsman
(74) Attorney, Agent, or Firm—Kenyon & Kenyon

(57) ABSTRACT

A process management system in accordance with the present invention includes inspection apparatuses for inspecting defects on a wafer, the inspection apparatuses being connected through a communication network, inspection information and image information obtained from these inspection apparatuses being collected to construct a data base and an image file, therein definition of defects is given by combinations of elements which characterize the defect based on the inspection information and the image information obtained from the inspection apparatuses. By giving definition of the defect, characteristics of the defect can be subdivided and known. Therefore, the cause of a defect can be studied.

10 Claims, 17 Drawing Sheets

U.S. PATENT DOCUMENTS

| | | | |
|---|---|---|---|
| 5,761,064 A | * 6/1998 | La et al. | 700/110 |
| 5,841,893 A | * 11/1998 | Ishikawa et al. | 382/145 |
| 5,991,699 A | * 11/1999 | Kulkarni et al. | 702/83 |
| 6,542,830 B1 | * 4/2003 | Mizuno et al. | 702/35 |

FOREIGN PATENT DOCUMENTS

| | | |
|---|---|---|
| JP | 48-39172 | 8/1973 |
| JP | 63-135848 | 8/1988 |
| JP | 03-044054 | 2/1991 |
| JP | 6-061314 | 3/1994 |
| JP | 06-275688 | 9/1994 |
| JP | 07-078019 | 3/1995 |
| JP | 07-505970 | 6/1995 |
| JP | 07-170280 | 7/1995 |
| JP | 07-201946 | 8/1995 |
| WO | WO96/26539 | 8/1996 |

TABLE OF MEMORY MAT POSITION COORDINATES AND DIRECTION INSIDE CHIP

| PIN NUMBER | PATH NUMBER | MEMORY MAT NAME | POSITION COORDINATES | DIRECTION |
|---|---|---|---|---|
| 1 | 1 ≀ 100 | MM1 | $(x_1, y_1)$ | ← |
|  |  |  |  |  |

TESTER (LOGICAL COORDINATE INFORMATION) — PIN NUMBER, PATH NUMBER

LAYOUT DESIGN (PHYSICAL COORDINATE INFORMATION) — MEMORY MAT NAME, POSITION COORDINATES, DIRECTION

FIG. 3A

MEMORY CELL ARRAY POSITION COORDINATES AND DIRECTION ON MEMORY MAT

| PATH NUMBER | MEMORY CELL ARRAY NAME | POSITION COORDINATES | DIRECTION |
|---|---|---|---|
| 1 ~ 10 | MA1 | $(x_2, y_2)$ | ↓ |
|  |  |  |  |

LAYOUT DESIGN

FIG. 3B

MEMORY CELL POSITION COORDINATES ON MEMORY CELL ARRAY

| Y-ADDRESS | X-ADDRESS | MEMORY CELL POSITION |
|---|---|---|
| 1 ~ 16 | 0 ~ 32 | $(C_o + C_x \times \text{Y-ADDRESS}, C_o + C_Y \times \text{X-ADDRESS})$ |
| | 32 ~ 63 | $(C_o + C_x \times \text{Y-ADDRESS}, C_o + C_Y \times \text{X-ADDRESS} - 32)$ |
|  |  |  |

TESTER (LOGICAL COORDINATE INFORMATION)

$C_x$ : X-DIRECTION SIZE OF MEMORY CELL
$C_Y$ : Y-DIRECTION SIZE OF MEMORY CELL

FIG. 3C

| CHARACTERISTIC ITEM | | CLASSIFICATION CODE | | 001 | 002 | ... |
|---|---|---|---|---|---|---|
| CHARACTERISTIC OBTAINED FROM IMAGE INFORMATION | SHAPE | SHORT CIRCUIT | ▨ | | | |
| | | LINE BREAK | ▨ | | | |
| | | PROJECTION (△) | ▨ | | | |
| | | CHIPPING-OFF | ▨ | ○ | | |
| | | PIN HOLE | ▨ | | ○ | |
| | | ISOLATION | ▨ | | | |
| | SIZE | WIRING WIDTH: BELOW 4/3 OF SPACE | | ○ | | |
| | | WIRING WIDTH: 1/3-2/3 OF SPACE | | ○ | | |
| | | WIRING WIDTH: ABOVE 2/3 OF SPACE | | | | |
| | ⋮ | ⋮ | | | | |
| CHARACTERISTIC OBTAINED FROM INSPECTION DATA | PROCESS PRODUCING DEFECT | RESIST PATTERN FORMING | PROCESS A | | ○ | |
| | | | PROCESS B | ○ | | |
| | | | ⋮ | | | |
| | | ETCHING PATTERN FORMING | ⋮ | | | |
| | DISTRIBUTION IN SURFACE | | | | | |

FIG.10

CLASSIFICATION OF DEFECT

EXTRACTING CHARACTERISTIC FROM REVIEW IMAGE INFORMATION

- PLAN SHAPE OF DEFECT ;
  CLASSIFYING BY SHORT CIRCUIT, LINE BREAK, PROJECTION, PIN HOLE, AND ISOLATION
- POSITION OF DEFECT IN LAYER ;
  CLASSIFYING BY SURFACE, IN PATTERN FILM, BETWEEN PATTERN FILM AND BASE FILM, AND IN BASE FILM
- DEFECT SIZE ;
  CLASSIFYING BY WIDTH : BELOW 1/3, 1/3–2/3, AND ABOVE 2/3 OF SPACE
- DEFECT COLOR ;
  DESCRIBING INTERFERENTIAL COLOR

EXTRACTING CHARACTERISTIC FROM INSPECTION INFORMATION

- PROCESS PRODUCING DEFECT ;
  DESCRIBING PROCESS NAME SUCH AS RESIST PATTERN FORMING, ETCHING, CVD, SPUTTERING AND SO ON
- APPARATUS PRODUCING DEFECT ;
  DESCRIBING APPARATUS NAME · CHAMBER NAME
- DEFECT SIZE ;
- CLUSTER CLASSIFICATION ;
- DISTRIBUTION IN DIE ;
- POSITION PRODUCING DEFECT IN DIE ;
  CLASSIFYING BY HIGH/LOW PATTERN DENSITY REGIONS, CELL/PERIPHERY REGIONS, GATE/WIRING REGIONS

EXTRACTING CHARACTERISTIC FROM DEFECT · FAULT ANALYSIS INFORMATION

- LAYER PRODUCING DEFECT ;
  DESCRIBING LAYER NAME
- CROSS-SECTIONAL SHAPE OF DEFECT ;
  CLASSIFYING BY FILM THICKNESS (THICK, THIN), COVERING (ASYMMETRY, OVERHANG), PRESENCE/ABSENCE OF VOID, AND SO ON
- COMPOSITION OF DEFECT PORTION ;
  DESCRIBING COMPOSITION CODE OR KEY WORD BY REFERRING TO AND COMPARING WITH LIBRARY
- STRUCTURE OF DEFECT PORTION ;
  DESCRIBING KEYWORD BY REFERRING TO LIBRARY

CLASSIFYING BASED ON DEFECT CLASSIFICATION TABLE

FIG. 11

EXAMPLE OF DISPLAY BY TOTAL ON CHIP-BY-CHIP BASIS

EXAMPLE OF DISPLAY BY TOTAL ON LOT-BY-LOT BASIS

PROCESS MANAGEMENT SYSTEM

This is a continuation of U.S. application Ser. No. 09/142,546 filed Sep. 10, 1998, now U.S. Pat. No. 6,542,830 issued on Apr. 1, 2003, which is a 371 of PCT/JP97/00898 filed Mar. 19, 1997.

BACKGROUND OF THE INVENTION

The present invention relates to manufacturing semiconductor devices or the like and, more particularly, to a process management system for a semiconductor manufacturing line with the aim of developing products in a short time and improving the yield.

A process management system of a semiconductor manufacturing apparatus is generally constructed in a client-server system. To an analysis station as the client and to a data base and an image file as the server, a wafer surface extraneous substance inspection apparatus and a pattern defect inspection apparatus for detecting defects produced on the semiconductor manufacturing line such as extraneous substance particles attaching on a wafer surface and pattern defects, an optical review apparatus for checking the detected defects, an SEM review apparatus and an FIB (focus ion beam) apparatus, and a probe inspection apparatus and a testing apparatus for testing operation (function, performance) of an LSI are connected through a communication circuit.

Inspection information obtained by the inspection apparatus and the testing apparatus is online collected into the data base, and image information on the process defects and LSI operating defect points obtained by the review apparatuses and the FIB apparatus is on-line collected into the image file.

The information on-line collected in such a manner is used for pointing out important defects, for diagnosing the defects and for taking a countermeasure against the defects.

In a system disclosed in Japanese Patent Application Laid-Open No. 3-44054, each of the probe inspection apparatus, the extraneous substance inspection apparatus, the visual inspection apparatus and the like has a data analysis station as a means for efficiently taking such a countermeasure. The analysis station is provided with arrangement information of chips on a semiconductor wafer defined on the kind-by-kind basis so as to have a function to judge which chip a defect or the like belongs to. Thereby, a situation of occurrence of defects and the like can be known on the chip-by-chip basis. Further, by connecting between the above-mentioned inspection apparatuses through a communication line, the situation of occurrence of defects and the inspection results of the defects can be understood.

Furthermore, the display mode of the output results is unified so that the output results are easy to be understood when the data is analyzed.

Further, Japanese Patent Application Laid-Open No. 48-39172 discloses a construction in which defects are classified on the type-by-type basis, and a predicted yield on the process-by-process basis is calculated from a probability of producing a defective semiconductor caused by each of the defect types and number of the defects.

The above-mentioned conventional technologies are insufficient to analyze the defects, and also insufficient to point out the defects and diagnose occurrence of the defects since number of items clarified as the result of the analysis is not so many.

In addition to this, there is a problem in that reliability of the predicted value of yield is low since the prediction of the yield is very rough.

SUMMARY OF THE INVENTION

An object of the present invention is to provide a process management system which is capable of effectively pointing out the defects and diagnosing occurrence of the defects and capable of predicting a highly reliable value of the yield.

1. The process management system in accordance with the present application has display modes as described below in order to perform data analysis.

(1) Distinguishing display based on data on wafers or chips:

According to the present invention, the distinguishing display for data analysis is performed based on various kinds of data on wafers or chips. Although the details are to be described in the section of Description of the Preferred Embodiments, the process management system of the present invention comprises the following display modes in order to more effectively point out the defects and diagnose occurrence of the defects.

Enlarged display based on defect inspection data

Display distinguishing between defects which have been reviewed and the other defects based on defect inspection data Display distinguishing between scribe lines and the other regions or between defects on the scribe lines and defects on the other regions based on data on the kind-by-kind basis of wafer Display distinguishing among regions having different characteristics obtained based on arrangement data of chips on a wafer Display distinguishing among regions having different distribution states of defects which are obtained from a defect inspection apparatus or the like Display distinguishing regions where a defect of the same kind is expected to repetitively occur on the region-by-region basis Display of a defect density map and a defect probability map Display recommending review positions for review work by combination of the various kinds of displays described above (2) Display on the inspection apparatus-by-apparatus basis and on a manufacturing process-by-process basis:

Display dividing between processes

Display tracing processes

Display of defects changing with process

Further, the following is provided in order to make the above displays clear.

(3) Function for setting definition of defect size.

2. Prediction of the yield of wafers or chips on the wafer:

The process management system of the present invention has the following elements in order to make highly reliable yield prediction possible.

According to the present invention, the process management system is connected to inspection apparatuses for inspecting at least defects on a wafer through a network to form a data base and an image file by collecting inspection information and image information obtained in these inspection apparatuses, and the management system comprises a means for classifying the defects on the basis of combination of elements characterizing the defects of a wafer, and a yield of the wafer or a yield of the chips on the wafer to the combination of elements is obtained based on a predetermined correlation table of yields of wafers or chips on the wafers to combinations of defective elements.

By the construction described above, the yield can be more strictly predicted based on the characteristics of defects since the defects can be classified in detail on the basis of the characteristic of defects.

Therein, it is preferable that the combinations of defective elements (defect classification) used in the correlation table are precisely set in a strong correlation with various kinds of faults as a premise. Further, the process management system of the present invention comprises a means for obtaining the strong correlation.

3. Data management:

In the present invention, the inspection data obtained from the various inspection apparatuses is managed by the following management means. The details are to be described in the section of Description of the Preferred Embodiments.

(1) Encipherment of inspection information
(2) Setting of management reference values
(3) Automatic reporting function
(4) Common download function

BRIEF DESCRIPTION OF THE DRAWINGS

FIGS. 3A, B, and C, show a conversion table of a logical positional coordinates—a physical positional coordinates of a memory LSI.

FIG. 10 is a view showing a corresponding table between defect classification code and defect characteristic item.

FIG. 11 is a flowchart showing a procedure of defect classification.

DESCRIPTION OF THE PREFERRED EMBODIMENTS

Figure 1:
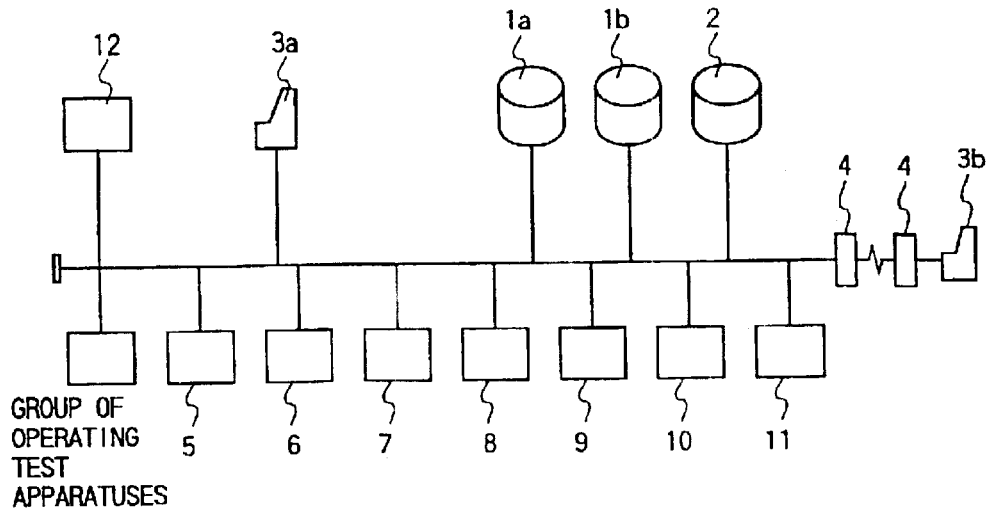
FIG. 1 shows an example of a system construction in accordance with the present invention.

FIG. 1 shows an example of a system construction. A client-server system is used in the system.

Analysis stations 3a, 3b and various kinds of inspection apparatuses and testing apparatus as the clients are connected to data bases 1a, 1b and an image file 2 as the servers by a communication network.

Each of the servers and each of the clients have functions described below. The data base server and the image server perform management (updating and retrieving) of inspection information stored in the data bases and image information stored in the image file. The analysis station performs reading out necessary stored data from the data bases and the image file, and forming and displaying the analyzed data. The inspection and the testing apparatuses acquire inspection information and image information, and input them into the data bases and the image file.

The inspection information and the image information are constructed, for example, as follows.

The inspection information is composed of various kinds of data on the kind-by-kind basis which are different from one another depending on the kind and various kinds of data on the wafer-by-wafer basis which are different from one another depending on the wafer.

The data on the kind-by-kind includes the following information.

Wafer size

Chip arrangement data; chip pitch, chip matrix

Chip pitch; chip size

Chip matrix; chip coordinates, chip name

Exposure field arrangement data; field pitch, field matrix, pitch matrix inside field Field pitch; field size Field matrix; field coordinates Chip matrix inside field; chip coordinates, chip name Inspection block arrangement data; block pitch, block matrix, chip matrix inside block Block pitch; block size Block matrix; block coordinates Chip matrix inside block; chip coordinates, chip name The data by wafer includes the following information Wafer data; lot number, wafer number, process name, processing apparatus name of the process and so on Inspection condition data; inspection apparatus name, inspection recipe name, management reference value, alignment pattern position coordinate data and so on Defect inspection data; defect number, defect size, defect position coordinates, defect classification code, review information and so on LSI operating test data; chip data, data of defect point inside chip and so on Wafer-by-wafer basis; chip coordinates, conforming item/defective item, defect classification code and so on Chip-by-chip basis; defect number, defective point position coordinates, defect number and so on The position coordinate data included in the operating test data is physical position coordinate data used in inspection which is converted from logical position coordinate data used in operating test. Conversion to the physical position coordinate data is performed using a position coordinate conversion interface. The interface is to be described later in detail.

The data base storing inspection information and the image file storing image information are constructed in a decentralized type, and are composed of the inspection data base 1a, the operating test data base 1b and the image file 2.

The operating test data server has the logical/physical position coordinate conversion function described above.

There are an analysis station 3a connected by a local area network and an analysis station 3b located in a remote site through a public communication line. Communication between the server and "the remote site analysis station 3b connected by the public communication line" is performed using enciphered data through an encipherer and a decipherer 4 placed between them.

The data transmission by encipherment is performed when data is transmitted to an external system (for example, to a client outside the local area network).

That is, in a case where data cannot help being transmitted through the public communication line though the remote site analysis station is placed in the common network, it is possible to prevent the data from leaking out of the public communication line by placing the encipherer and the decipherer in the public communication line.

The inspection data is secret information which should be kept from the outsider since a manufacturing scale and a yield of a semiconductor manufacturing line can be easily estimated from the quality and the quantity of the inspection data. On the other hand, the inspection data is meaningless if it is not retrieved and analyzed by many engineers engaged in improving yield in a lot of semiconductor manufacturing lines in order to effectively improve the yield. The essential elements described above are particularly effective for preventing leakage of the inspection data information which is retrieved and used at many sites though it is secret information.

An aspect of an embodiment of the present invention will be described in detail below, referring to a semiconductor manufacturing line having inspection/testing apparatuses and groups of pattern forming apparatuses as shown in FIG. 1.

The inspection apparatuses and the testing apparatuses are a group of wafer outer appearance inspection apparatuses 5 such as an SEM type pattern defect inspection apparatus and the like, a group of worked pattern inspection apparatuses 6 such as a pattern dimension measuring apparatus, a pattern superposing inspection apparatus and so on; a group of formed film inspection apparatuses 7 such as a film thickness measuring apparatus, a film composition measuring apparatus, a film characteristic measuring apparatus and so on; a group of ion injected state inspection apparatuses 8 such as dopant concentration measuring apparatus, a dopant profile measuring apparatus and so on; a group of reticle related apparatuses 9 such as a reticle extraneous substance inspection apparatus, a reticle defect correction apparatus and so on; a group of physical analyzing apparatuses 10 such as a TEM, an AES, a SIMS and so on; a group of fault rescuing apparatuses 11 such as a wiring correcting apparatus for correcting a wiring pattern formed on a wafer and so on; and a group of pattern forming apparatuses 12. The pattern forming apparatus 12 has a function to transmit pattern design information such as a pattern density and so on to an analysis station corresponding to request from the analysis station.

Further, a review apparatus (an apparatus for precisely inspecting defects by forming a defect image) for classifying the defects so as to be easily analyzed is also connected to the communication network.

The inspection data obtained by each of the inspection and the testing apparatuses is added with additional data such as kind data, wafer data and so on, and is input and stored in the data base as inspection information. The data base server performs retrieval and updating of the inspection information.

The data on the kind-by-kind basis, the wafer data and the inspection data are commonly used in each of the inspection and the testing apparatuses. Each of the inspection and the testing apparatuses can read out and use the data on the kind-by-kind basis, the wafer data and the inspection data from the data base by specifying them. In a semiconductor manufacturing line in which frequency of changing in the process conditions is high and many apparatuses of the same kind are used, the essential element of download is particularly effective for decreasing work at changing the condition and preventing occurrence of faults caused by a mistake in the changing.

The inspection data stored in the data base is used ① for forming analysis data in the analysis station and ② for observing and analyzing defects precisely using the review apparatus and the physical analyzing apparatus.

Description will be made below on ① the forming of analysis data and ② the observing and analyzing defects using the review apparatus.

① Regarding the Forming of Analysis Data

The analysis stations 3a, 3b are apparatuses for forming the analysis data described above, that is, for forming and displaying (1) wafer outer appearance analysis data, (2) yield analysis data and (3) wafer outer appearance—yield correlation analysis data.

Figure 7:
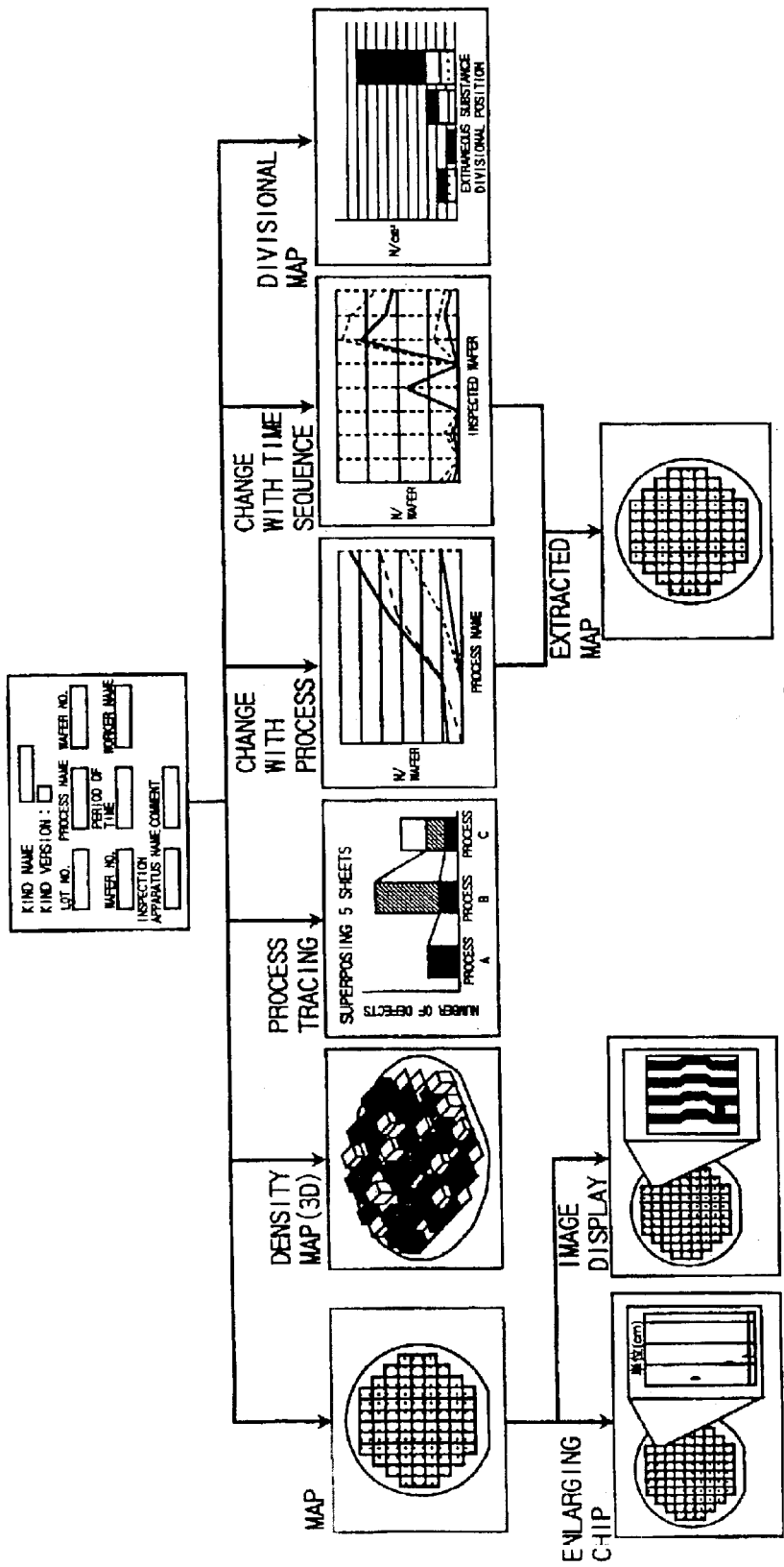
FIG. 7 is a block diagram showing an example of displays of analysis data in a wafer outer appearance analysis.

(1) Wafer Outer Appearance Analysis Data:

FIG. 7 shows an example of a display of analysis data in wafer outer appearance analysis. The wafer outer appearance analysis data is data on defect distribution and on change in occurrence of defects formed and displayed based on the inspection data. The wafer outer appearance analysis consists of functions of defect map, defect density or defect probability map, change of defects with process, defect level management in addition to data base retrieving.

Here, the defect is defined as follows. That is, in regard to a defect having a problem in "existence" such as an extraneous substance particle attached on a wafer surface, a pattern defect, an extraneous substance particle attached on a reticle, a reticle defect correction mark and a wiring correction mark, a state in which the "existing type defect" exists on a wafer or a reticle is defined as a defect. In regard to a defect having a problem in a "state" such as a pattern dimension, an accuracy of pattern overlapping, a film thickness of a formed film, in-film stress of a formed film and a dopant concentration, a state in which a measured value of the "state type defect" is out of a range of specification is defined as a defect.

A magnitude of the existing type defect is expressed by size, and a magnitude of the state type defect is expressed by a measured value.

In regard to a defect in connection with a reticle such as an extraneous substance particle attached on a reticle or a reticle defect correction mark, a value converted on a wafer is used as the size or the measured value. In regard to a defect expressed by a vector among the state type defects such as an accuracy of pattern overlapping is expressed by dividing the measured value into a magnitude and a direction or an x-component and a y-component.

In order to displays shown in FIG. 7, the following process is performed.

Initially, an analysis range, that is, an inspection data retrieving range is specified by specifying wafers to be analyzed with AND conditions using a kind name, a lot number, a process name, a wafer number, a period of time, an inspection apparatus name and so on. By doing so, data in connection with the specified wafer is retrieved from the data base and read out to the buffer memory.

Next, a requested display format of the analysis data (a graph format such as a map, a chart of change with process and the like and items and scales of the ordinate and the abscissa and so on) is specified.

Thus, necessary analysis data can be displayed on a screen using the above-mentioned retrieved data. An enlarged view of chip and a defect image can be extracted from the map, and a map of a specified wafer (an extracted map) can be also extracted from the chart.

Further, information for tracking down cause of a fault or cause of occurrence of defects can be obtained from a checking map, for example, information in connection with fatality of defects can be obtained by checking a defect map with a yield map of the same wafer, process tracing of defects can be obtained by checking a defect map of process A with a defect map of process B of the same wafer, repetitive defect information can be obtained by checking a defect map of the wafer A with the defect map of the wafer B of the same process.

In this embodiment, checking of various combinations can be performed since based on the inspection information the other inspection information and image information are managed. FIG. 7 is such an example of display.

Examples of various kinds of displays of wafer outer appearance will be described below in detail.

(1-a) Defect Map:

A defect map is formed by plotting a result retrieved from the inspection data base on a wafer map to make a defect state on the wafer visually clear.

In this embodiment, the display units are provided in the analysis stations $3a$, $3b$ of the system shown in FIG. 1, and inspection data read out from the data base or the image file based on designation of various conditions is displayed on a specified region such as a wafer or a chip displayed on the display unit.

The designation of various conditions will be described below in detail.

(1-a-1) Designation of Display Condition:

(a) Designation of Classifying Condition:

Defect inspection data is selected from the following condition to be displayed. In a case of plural designations, the condition is expressed by AND condition.

(I) Wafer classification: ① all wafers, ② wafers in the same lot, ③ classification on the specified wafer basis.
(II) Process classification: ① all processes, ② classification on the specified process basis, ③ a process at present time, ④ processes before the process at present time.
(III) Defect classification: ① all defects, ② fatal defects, ③ non-fatal defects.

(b) Designation of Condition on the Category Basis:

Defect data belonging to a specified defect classification code is displayed. The specified defect classification code is to be described later.

(c) Designation of Condition of Defect Size/measured Value:

Defect data fitting to a specified range of size/measured value is displayed.

Designation of the range of size/measured value is performed by selecting one out of ① an upper limit, ② a lower limit, ③ a specified range.

In regard to definition of the size, an item is selected from the following by setting a length of a defect in x-direction in a wafer coordinate system to X and a length of the defect in y-direction to Y. The defect size used is an item of data obtained from the extraneous substance inspection apparatus or an item of data obtained from the review apparatus, and registered as defect inspection data.

① size=√(area of defect)
② size=√(defect length X)×(defect length Y)
③ size=√[(defect length X)$^2$+(defect length y)$^2$]
④ size=Max [(defect length X), (defect length Y)]
⑤ size=(defect length X)
⑥ size=(defect length Y)
⑦ size∝function of (defect detecting signal intensity)

(d) Designation of Check:

A plurality of results of analysis data are displayed by overlapping. The following checks are available.
① defect inspection data—defect inspection data
② defect inspection data—operating test data
③ operating test data—operating test data In regard to display of the defect inspection data—defect inspection data check, the checking condition and the checking method are designated as follows.

(I) Kinds of Defects to be Displayed by Overlapping:

① an extraneous substance particle attached on a wafer surface, ② a pattern defect, ③ a pattern dimension, ④ a pattern overlapping accuracy, ⑤ a film thickness of a formed film, ⑥ an in-film stress of a formed film, ⑦ a dopant concentration, ⑧ an extraneous substance particle attached on a reticle, ⑨ a reticle defect correction mark, ⑩ a wiring correction mark and so on.

It is possible to check between the same items each other. For example, checking defect size with defect size, or pattern dimension with pattern dimension. The checking of this kind makes it possible to check difference between the inspection apparatus and the testing apparatus, change with time in performances of the inspection apparatus and the testing apparatus, performance of inspected wafer dependence and so on, and is a particularly effective means to realize an accurate inspection.

(II) Data Retrieving Condition

Objective wafer: ① all wafers, ② wafers in the same lot, ③ the same wafer.
Objective process: ① all processes, ② a process at present time, ③ processes before the process at present time, ④ retrieval on the process basis.
Objective inspection apparatus: ① all apparatuses, ② retrieval on the specified apparatus basis
Objective defect size or measured value: ① all defects or all measured values, ② an upper limit value, ③ a lower limit value, ④ a range.
Objective defect type; ① all defects, ② fatal defects, ③ non-fatal defects, ④ defect on the classification code basis.

(III) Checking Condition and Checking Method

Allowable deviation range at comparing coordinate data: ① an upper limit.
Checking method: ① OR, ② AND, ③ XOR.
Displays of checking of ① the defect inspection data — operating test data and checking of ② the operating test data—operating test data are to be described later.

Figure 18:
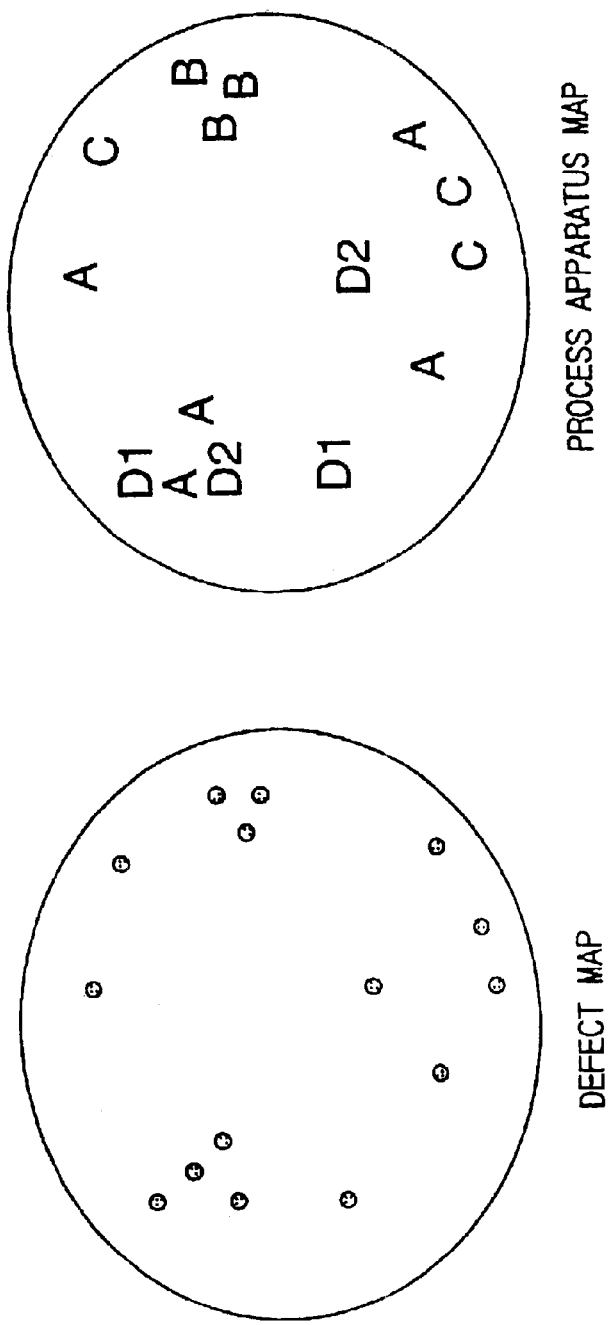
FIG. 18 is a view showing an example of defect inspection data displayed as a defect map.

According to this embodiment, the defect inspection data can be displayed as a defect map based on the above-mentioned designated conditions. For example, when the ④ retrieval on the process basis is selected as the objective process in the above-mentioned designation, a display as shown in FIG. 18 can be obtained.

These designations are performed in the analysis stations $3a$, $3b$, and inspection data is read out from the data base or the image file based on the designations and output based on fixed-formed display forms (map display, chart display and so on, the various display forms described in the present specification).

Further, in order to make the defect analysis easy and accurate, the following special display functions are provided.

(1-a-2) In-wafer and In-chip Divisional Designation Displays:

As described above, the inspection data taken by the inspection apparatus is displayed on the display unit such as a CRT as a defect map.

At that time, some defects are fatal defects and the others are not fatal defects depending on positions where the defects exist even if the defects are similar. Further, there are some defects which need to be observed in detail and the others which do not need to be observed in detail. If these matters can be visually distinguished, the defects can be correctly classified and accordingly extra review (details of the review are to be described later) becomes unnecessary. Thereby, it is possible to speedy improve the yield and increase the work efficiency in the semiconductor manufacturing line.

Examples of the display forms will be described in detail below.

(a) Enlarged Display:

This is a function to enlarge and display a specified area on a wafer map. A part of the defect map is displayed.

In more detail, for example, a specified chip is enlarged and displayed (the display shown in a lower left-hand part of FIG. 7). It is convenient to judge the fatality of a concerned defect and to extract and display a defect image taken by a scanning electron microscope (SEM) or the like.

Further, by enlarging and displaying an image on the exposing field basis of a step-and-repeat equipment (a light exposing equipment), it is possible to accurately specify a position of a repetitive defect produced at pattern forming by light exposure (at reticle pattern transferring to the wafer). Therefore, it becomes easy to perform feed-back to cleaning of the reticle and to judge the fatality of defect. This case is based on exposure field arrangement data registered as data on the kind-by-kind basis.

Furthermore, it is possible to enlarge and display on the block-by-block basis by dividing the chip arrangement by the predetermined inspection block basis of the defect inspection apparatus.

(b) Reviewed Defect Display:

A semiconductor wafer becomes a product through various treatment processes, and there are inspection processes for quantitatively inspecting produced defects between the treatment processes. Further, there is review work for confirm whether or not the inspection is properly performed. The review is generally performed on pre-targeted defects, but used for analysis work to be performed later by making it possible to judge which defect has been reviewed.

In this embodiment, in order to attain such an object, reviewed defects are distinguished and displayed on a defect map so as to be capable of being distinguished. The distinguishing method considered is, for example, to use different color or shape for marks indicating defects.

As a practical example, when a concerned defect image is required to be seen during analysis work, it is possible from the 'reviewed defect display' attached to the defect on the map to judge whether or not the defect review image has been already taken. If the defect review image has been already taken, the defect image can be extracted and observed on the spot. Capability of performing the above-mentioned processes depends on that the analysis stations 3a, 3b and the data base and the image file of FIG. 1 are connected to the communication network and the history of review is stored in the defect inspection data.

(c) Scribe-line Display:

The scribe-line is a line-shaped area between chips where no active pattern exists. The wafer is finally cut into individual chips, and the scribe-line is, as it were, a margin left for the cut. That is, a defect on the scribe-line cannot be a fatal defect even if the defect exists. Further, performing work such as review on such a defect is useless and results in decreasing work efficiency.

In this embodiment, the problem described above can be eliminated by displaying the scribe-line or defects on the scribe-line in distinguishing from the other area on the wafer or the other defects.

Methods of the scribe-line display considered are to display the chip arrangement data registered in the data base or the image file of FIG. 1 together with the defect map as wafer data on the kind-by-kind basis, or to compare defect position information obtained from the defect inspection apparatus with scribe-line position information of chip arrangement data and then specify and display positions where the both agree.

(d) Area-by-area Basis Display:

By designation of an operator using a pointing device or the like on the display unit or by designation of area based on the arrangement data registered in the data base or the image file of FIG. 1, defects in the each designated area are displayed so as to be distinguished.

In a case of a memory cell LSI, a memory cell area is displayed with distinguishing from a circuit area in the periphery. The circuit area in the periphery has a lower pattern density compared to the memory cell area and accordingly has a relatively smaller probability of a defect causing a fault. On the other hand, there are some cases where a fault of the memory cell can be rescued depending on the fault condition. By displaying the both areas with distinguishing from each other, it is possible to take measures such as classifying defects or selecting a review position to cope with similar defects in the both areas even if the similar defects exist.

That is, it is easy to determine a measure of inspection or review.

The same effect as described above can be attained by doing the distinguishing display between a gate area and an inter-gate wiring area of a gate array.

The distinguishing display is performed based on, for example, chip arrangement data which is registered in the data base or the image file of FIG. 1 as the wafer data on the kind-by-kind basis. It is acceptable that defects in the memory cell area and defects in the peripheral circuit area are displayed so as to be respectively distinguished from each other. In this case, the defect position information obtained from the defect inspection apparatus is compared with the above-mentioned chip arrangement data.

Further, an effect similar to that described above can be attained by doing the distinguishing display on the pattern density basis. In this case, pattern density distribution data in chip is registered as wafer data on the kind-by-kind basis in advance.

Further, it is acceptable to distinguish on the basis of inspection sensitivity of the inspection blocks. In general, there is limitation determined by the maximum noise area inside an inspection area. A lower importance and larger noise area is omitted from areas to be inspected in order to perform highly sensitive inspection. By displaying the lower importance and larger noise area with distinguishing from the other areas, it is possible to omit unnecessary review work and the like.

An example of such an area (called as a non-inspection area) is a memory mat edge in a memory LSI.

(e) Clustering Display:

Clustering (gathering) defects or an area where clustering defects exist are distinguished and displayed out of image data obtained from the defect inspection apparatus.

The clustering defects have a high possibility to cause a fault. Further, in general, the clustering defects are, in most cases, produced by the same cause of defect. That is, characteristics of all the defects in the cluster can be clarified by picking up and reviewing a specified defect among the clustering defects.

In this embodiment, in order to make the work easy, when a cluster state of defects is above a preset condition by judging the cluster state, the defects or the existing area of the defects are distinguished and displayed. For example, in a case where areas having number of defects above a preset value are continuously exist within a certain area, or in a case where defects adjacent to each other continuously exist within a preset spacing, the group of defects is recognized as clustering defects to be distinguished and displayed.

Therein, the recognition and the distinguishing of clustering defects are performed by the defect inspection apparatus or the review apparatus and the clustering defects are registered in the data base, or performed by the analysis station.

(f) Repetitive Defect Display:

In this embodiment, defect positions are compared on the chip basis, on the exposure field basis or on the inspection block basis, and defects repetitively appearing at a position in the same coordinates are judged and displayed as repetitive defects.

The judgment and the display are performed based on defect coordinate data obtained by the defect inspection apparatus or the like.

By the display and the judgment, it is possible to verify, for example, a pattern defect of the step-and-repeat equipment (the light exposing equipment) for transferring a circuit pattern by continuously repeating exposure, a defect caused by the reticle and an erroneous detection caused by the inspection apparatus.

For example, a reticle correction mark has a small lithography margin and accordingly is apt to cause a pattern transfer fault. In the highly sensitive inspection at the performance limit of the inspection apparatus, small unevenness in the sensitivity causes erroneous detection. Since the erroneous detecting portion often repetitively appears, in order to eliminate the erroneous detection caused by the inspection apparatus, inspection data is dealt by dividing into inspection blocks so as to be judged and displayed. The inspection block means a repetitive unit in comparative inspection.

In detail, the defect coordinate data obtained is divided based on exposing field arrangement data registered in the data base 1 of FIG. 1, and items of defect coordinate data on the basis of the divided partial coordinate system are checked with one another. When number of defects regarded agreeing in the coordinate positions is large, the defects are distinguished from the other defects and displayed as repetitive defects. This processing is performed on the analysis stations 3a, 3b.

(1-a-3) Inter-process Dividing Designation Display:

A semiconductor wafer manufacturing line has a plurality of treating processes and many inspection processes each of which is placed between the treating processes. Inspection data is obtained in each of the treating processes.

The inspection data is attached with inspection information and registered in the image file 2 and the data base 1 shown in FIG. 1. The inspection data is registered on the process-by-process basis of inspection. That is, by displaying the inspection data on the process-by-process basis of inspection, it is possible to confirm change of defects in each of the treating processes. Thereby, it is easy to specify which process defects are produced in, and it is possible to cope with measures to eliminate the defects. The details will be described below.

(a) Process Tracing Display:

In regard to a defect on a wafer, whether the defect is produced in a process before a process at present time is traced and studied by comparing each defect coordinate data of each inspection process. That is, defect coordinate data of a wafer is compared with defect coordinate data of the same wafer obtained in a process before the process at present time. If there is a defect agreeing in the coordinates within a preset range, the defect is regarded as the same defect. It is considered that the defect regarded as the same defect is produced in a process before the process at present and affects the present process.

By displaying the result as shown in FIG. 7, it is possible to specify what defect is produced in which process.

(b) Display of Defect Produced in the Present Process:

In regard to a defect on a wafer, whether the defect is produced in a process at present time is traced and studied by comparing coordinate data of each defect. That is, the defect produced in the present process is distinguished from the other defects and displayed.

(1-a-4) Review Position Display:

In a recent semiconductor manufacturing line, a review is performed to judge whether or not inspections performed in inspection processes are appropriate. However, since it takes a very long time to perform the review for all the defects, it is necessary to select defects to be reviewed in advance. If the selection is improperly performed, reliability of the data obtained using a very long time is decreased and there occurs a problem in that the data does not reflect the actual state.

Description will be made below in detail on an example of a display for supporting the selection of appropriate review positions.

Therein, the review is performed according to the procedure of detection of defects, exclusion of false defects and classification of defects in order to point out defect and clarify cause of occurrence of the defects. The exclusion of false defects means excluding an event that a phenomenon actually unacceptable as a defect is erroneously detected as existence of a defect.

Figure 5:
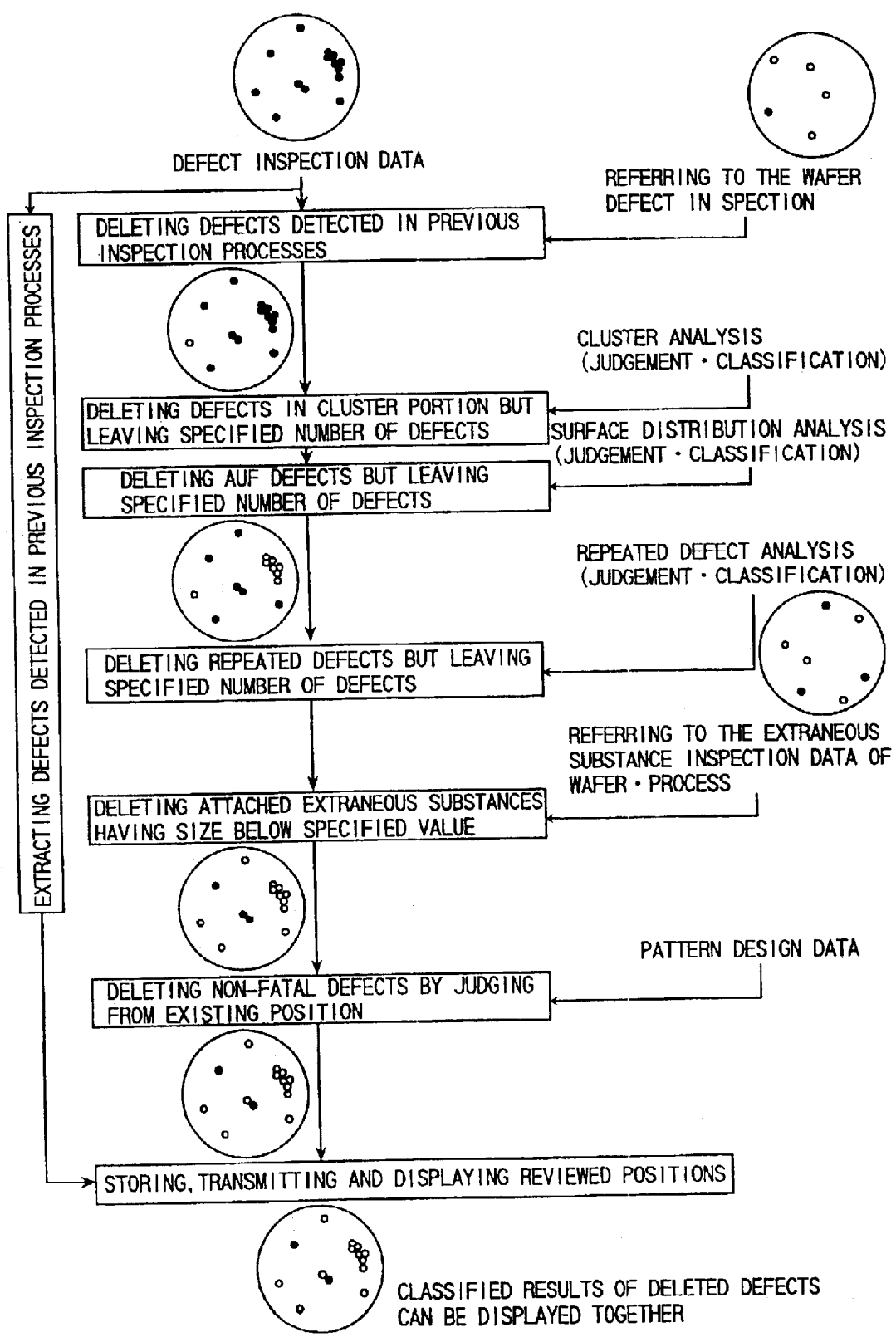
FIG. 5 is a block diagram showing a procedure of detecting and reviewing defects.

Recommended review positions are automatically selected and displayed. The selection is performed according to the procedure shown in FIG. 5.

① Deleting defects produced in processes before the present process.

② Performing clustering judgment, and deleting defects in a cluster portion but leaving specified number of defects.

③ Judging repetitive defects on the chip basis, on the exposing field basis and the inspection block basis, and deleting the repetitive defects but leaving specified number of defects.

④ Checking with extraneous substance data, and deleting defects which agree in coordinate positions and are smaller than a specified size.

⑤ Judging defect positions, and deleting defects estimated as non-fatal defects.

The judging method is specified one from the following.

Judging pattern densities, and deleting defects in a position having a specified pattern density lower than a specified pattern density.

Judging isolation degrees, and deleting isolated defects.

Memory LSI: Judging whether a defect is in a memory cell area or in the peripheral circuit area, and deleting the defects in a peripheral circuit area.

Gate array: Judging whether a defect is in a gate area or in a wiring area, and deleting the defects in the wiring area.

⑥ Displaying the remaining defects as recommended review position.

The above processes ① to ⑥ are the processes described in the items of (1-a-2) In-wafer/In-chip divisional designation display and (1-a-3) Inter-process dividing designation display.

The above procedure is arranged in order of low review recommending degree, but the order is not limited to this order. Further, it is not necessary to employ all of the processes ① to ⑥, but it is possible to employ one of the processes or a combination of two or more of the processes.

On the other hand, from the viewpoint that an important problem is a defect affecting the following processes, defects produced in the processes before the present process are displayed as sampling positions.

The defect detecting work needs to be performed at as high sensitivity as possible so as to not miss serious defects, but number of erroneously detected defects, that is, number of false defects is increased and the review work becomes more difficult as the sensitivity is increased. However, according to the construction described above, number of defects to be reviewed is reduced and the review work can be simplified.

(1-a-5) False Defect Judging Means at Reviewing:

The example in which efficiency of the review work is improved by displaying review recommended positions in the preceding item. However, one of the reasons to make the review work difficult is that the review work cannot help performing using an SEM though defects are optically detected.

In the present time, a defect having a size of 0.2 µm can be detected using an optical means. However, since maximum resolution of an optical microscope is about 0.2 µm, review using the optical microscope cannot distinguish shape and color of a detected fine defect. Therefore, SEM review is widely employed instead of optical review.

However, an SEM image is different from an optical image in contrast forming mechanism. In the SEM image different from the optical image, what can be seen is only the surface shape, and color and brightness information is not included. Therefore, in a case where optically detected contrast in a defect is caused by the internal structure or the difference of color and brightness, the SEM review cannot recognize these factors, and cannot judge and review the false defects correctly.

For example, in a case where thickness of a silicon oxide film is uneven on a wafer surface, optical unevenness of color appears by interference inside the film. In a method of comparing two images (for example, images of two chips to be compared in the same position) of an optical pattern defect inspection apparatus, a process defect is detected by detecting the difference between the two images in color and brightness caused by the unevenness of color.

On the other hand, in a case where the defect is reviewed using the SEM, no abnormality is observed in that position and accordingly the defect position cannot be detected because the SEM image cannot detect the unevenness of color and the film thickness.

Since the pattern defect inspection apparatus is of a high throughput, an optical image comparing method is used.

Therein, if there exist difference in pattern shape and/or image contrast caused by variation in pattern dimension and position on the surface, difference in interference color caused by variation in film thickness on the surface, change in light reflectance caused by distribution of a doped impurity over the surface, a wiring correction mark and so on, these are detected as defects. However, the defects include many defects to be classified into the false defects.

In order to judge the false defect correctly and speedy using these factors as reference information at SEM review, data on the variation in pattern dimension and position, the variation in film thickness, the variation in the doped impurity, the wiring correction mark and so on is online collected and stored in the data base. Then, the data is read out at SEM reviewing to be displayed at a time on the display unit provided in the analysis station.

(1-a-6) Simplification of Defect Classifying Work:

In the present invention, defects are classified at reviewing.

Details of the defect classification is to be described later. Since there is provided a means for classifying defects on the basis of combination of a plurality of elements expressing characteristics of the defects, it is easy to specify a factor of producing defects. That is, when defects are classified according to classification code as shown in FIG. 10, it is easy to study what cause a defect is produced by because characteristics of the defect can be subdivided and known.

For example, in a case where an element "short circuit" is observed out of characteristics obtained from the screen information of FIG. 10, it can be considered that the cause of producing the defect is halation due to "spread" caused in the light exposure equipment.

It is difficult to specify characteristics of defects because various kinds of elements are complex. However, in the present invention, the specification of defects can be made easy by classify the characteristics of the defects in detail. This effect can be attained by display each of the elements of the selected defects on the display unit of the analysis station 3 as shown in FIG. 10.

By reading out each of the elements obtained at reviewing from the data base using defect selection on the display unit, an operator can make the above-mentioned judgment based on the display. The details are to be described later.

(1-b) Defect Density and Defect Probability Maps:

The defect density means a degree of closeness of defects on a wafer or a chip.

As described above, the existing type defect is such a defect that the existence itself is problem, and number of the defects becomes a factor to affect the final yield. That is, if a defect density is known, it is possible to determine a yield to a certain degree based on an empirical rule and accordingly the defect density is effective. On calculating a defect density, the defect density is calculated by dividing a total number of defects existing in a certain region by an area of the certain region.

The detailed construction of calculating such a defect density is that number of defects, for example, on a region specified by the pointing device or the like on the display unit provided in the analysis station 3a or 3b of FIG. 1, or a region specified by arrangement data registered in the data base 1 as inspection data or an area value input from the analysis station 3a or 3b is divided by an area of the region. The area of the arrangement data registered in the data base is registered, for example, as a chip size.

An example of a map display of the defect density is shown in FIG. 7 (the density map of the second frame in left hand side).

In this example of display, defect densities on the chip-by-chip basis are displayed. In this case, number of defect obtained by the wafer outer appearance inspection apparatus group 5 of FIG. 1 or the like and registered in the data base 1 is divided by a chip size also registered in the data base, and then the value is displayed on a wafer map displayed on the display unit of the analysis station 3a or 3b. In the example of FIG. 7, each of the densities is displayed on each of the chips with a histogram based on a height of the density. By this display, it is possible to confirm the defect density on the chip-by-chip basis at a glance and to study a trend of number of produced defects to each of the positions on the wafer.

On the other hand, the defect probability means a probability expressing what number of values deviating from a reference value exists in number of measured values in a chip of a specified process parameter, that is, what number of defects exists in number of measured points inspected. As for the state type defect, the "defect" is a defect deviating from a certain reference, and the other defects are not regarded as the "defect". The defect probability is effective in confirming the state type defect in which a state such as pattern dimension or film thickness is problem. The state type defect is a defect in which the problem is a degree of a state such as pattern dimension but not presence of an extraneous substance particle or a pattern defect as described above. The yield depends on not only the existing type defect such as a pattern defect or an extraneous substance particle but also the state type defect such as pattern dimension. If defects are determined from the viewpoint of the existing type defect in spite of the above fact, it is impossible to attain improvement of the yield which is the final object of defect detection.

The result is displayed in such a manner as the defect density map described previously.

Taking a case of the map of the second frame in left hand side in FIG. 7 as an example similarly to the density map, defect probabilities on the chip-by-chip basis are displayed in this example. By this display, it is possible to confirm the defect probability on the chip-by-chip basis at a glance and to study with what degree of probability problem defects exist in each of the positions on the wafer.

The examples of three-dimensional display are described above, but two-dimensional display may be acceptable. Further, selection of the display conditions described in the above item of defect map may be employed. For example, the display conditions are specification of condition on the kind basis, specification of condition on the category basis, specification of defect size/measured value condition, specification of in-wafer/in-chip dividing and so on.

These specifications are performed on the analysis station 3a or 3b, and the above-mentioned specifications of condition are displayed mainly on the display unit so as to select one out of them. Data necessary for a selected display is read out from the data base 1 based on the selected display condition to be displayed.

The specification of the display condition is performed using the keyboard, the pointing device or the like provided in the analysis station 3a or 3b.

(1-c) Display of Change of Defects with Process:

The display of change in number of defects with process shows change in number of specified kind defects as the process is changes by taking the process in the abscissa.

In the embodiment of the present invention, there is provided an original display form of the present invention in addition to the display of change of defects with process disclosed in Japanese Patent Application Laid-Open No. 3-44054.

In the present invention, there is also provided a function to chart-display number of defect, defect density or defect fault ratio on a wafer or a chip for the existing type defects described previously, and to display number of defect, defect density or defect fault ratio for the state type defects.

By the display, in a case of the existing type defect, defects produced in the present process and defects produced in processes precedent to the present process can be separated and displayed by comparing positions on a wafer of defects produced in each of the processes.

On the other hand, in a case of the state type defect, mutual validity of a resist pattern inspection process and an etching pattern inspection process can be checked by comparing change of defect states in the dimension inspection process for resist pattern and the dimension inspection process for etching pattern. As described above, an appropriate display corresponding to this embodiment can be performed.

According to the present embodiment, in order to realize such a display as described above, whether the existing type defects or the state type defects are displayed is predetermined corresponding to a process to be inspected or an inspection apparatus used. In detail, defect information obtained by as apparatus for inspecting a "state" of defects comprises a means for judging and specifying defect information obtained by an apparatus for inspecting "existing" of defects based on inspection conditions and data registered in the data base. This judging and specifying is performed on the analysis station 3a or 3b.

The specified result is registered in the data base or image file as defect inspection information.

Further, in a case of selecting defects based on what kind of process the defects are produced, the selection is performed by specifying whether the defects are produced after a process capable of producing the existing type defect or the defects are produced after a process capable of producing the state type defect. Then, the selecting information is registered in the data base as the defect inspection data. After that, the above-described chart display is performed based on the registered data.

According to the embodiment of the present invention, number of defects, a defect density, a defect fault ratio, a measured value, a defect probability of the existing type defect and the state type defect are determined based on the following calculation equations.

number of defect=(number of defects excluding erroneously detected defects).

defect density=(number of defect)/(inspected area per chip)×(number of inspected chips).

defect fault ratio=(number of chips having defects)/(number of inspected chips).

defect probability=(number of defect)/(number of inspections)×(number of inspected chips).

As described in the item of defect map, the defect inspection data can be displayed as data of change of defect with process based on the following specifying conditions.

1. Display on the kind basis.
2. Display on the category basis.
3. Display on the size or measured value basis.
4. Display on the region basis.
5. Process tracing display.

In regard to defects on a wafer, whether or not the defects exist in processes before the present process is traced by comparing coordinate data of each of the defect, and the result is displayed in a form of a divided chart or a gallery.

In the display of divided chart, "process name" specified in a retrieving condition is taken in the abscissa, and "number of defects" is taken in the ordinate for a case of the existing type defect and "measured value" for the case of the state type defect.

A chart is displayed according to the selection.

Retrieving conditions other than the process name are to specify an objective wafer, an objective inspection apparatus, an objective defect size or measuring value, a range, an objective defect kind and an allowable deviation range at comparing coordinate data.

6. Display of defects produced in the present process:

In regard to defects on a wafer, whether or not the defects are produced in the present processes is traced by comparing coordinate data of each of the defect detected in the processes before the present process, and the result is displayed in a form of a divided chart or a gallery.

In the display of divided chart, number of defects, defect density or defect fault ratio is taken in the ordinate for a case of the existing type defect and measured value, defect probability or defect fault ratio is taken in the ordinate for the case of the state type defect, and total processes, the present process or processes before the present process is taken in the abscissa. An upper limit of the allowable deviation range at comparing coordinate data is specified as a condition.

(1-d) Defect Level Management Display:

In the defect level management display, number of defects, defect density or defect fault ratio for a case of the existing type defect and measured value, defect probability or defect fault ratio for the case of the state type defect is taken in the abscissa as classification interval number, and number of wafers within the classification interval number is taken in the ordinate, and the result is displayed in a form of a chart.

In another form of the defect level management display, period, wafer or lot is taken in the abscissa, and number of defects, defect density or defect fault ratio is taken in the ordinate for a case of the existing type defect and measured value, defect probability or defect fault ratio for the case of the state type defect, and the result is displayed in a form of a chart.

As described in the items of defect map and display of change of defects with process, the defect inspection data can be displayed as data of change of defect with process based on the following specifying conditions.

1. Display on the kind basis.
2. Display on the category basis.
3. Display on the size or measured value basis.
4. Management reference value display.

A management reference value and statistically processed values such as an average value and a deviation are displayed.

Further, a display method is selected one from graph display and numerical display. Setting of the management reference value is selected one from the following two.

Displaying values stored in the data base as the inspection data.

Automatically setting and displaying statistically processed values of the stored inspection data.

At that time, the following condition is further specified.

The processing range is selected any one out of a period before the time point of calculation, cumulated processed lots and number of cumulated processed wafers. The displayed value is selected any one out of average value and average value/deviation. The automatic setting is performed on number of defects for the existing type defect and deviation for the state type defect. The automatically set management reference value is automatically unloaded to a related inspection apparatus by specification.

In the embodiment of the present invention, when the input inspection data exceeds the management reference value or a fluctuation state deviates from a specified reference, an alarm is set so as to automatically sound.

The specified reference is selectively specified any one of the following.

1. A specified Cp/Cpk value is specified as a reference.
2. In a case of occurrence of a special distribution—where defect occurring frequency of a special chip is high or defect occurring frequency of a special position in a chip is high, alarm is sounded when the state exceeds a certain level.
3. When the management reference value deviates from an allowable defect occurrence frequency, alarm is sounded.
4. When a measured value of defects or process parameter is continuously fluctuated within a specified period, alarm is sounded. In a case of the existing type defect, alarm is set so as to sound, for example, when the above-mentioned parameter on the existing type defect is in a increasing trend. In a case of the state type defect, alarm is set so as to sound, for example, when the above-mentioned parameter on the state type defect is in a increasing or decreasing trend.

According to this embodiment, a defect chart or a map in a specially specified classified interval or specified time can be displayed.

Further, a report on a specified item is issued with a predetermined time interval and a predetermined format.

Figure 8:
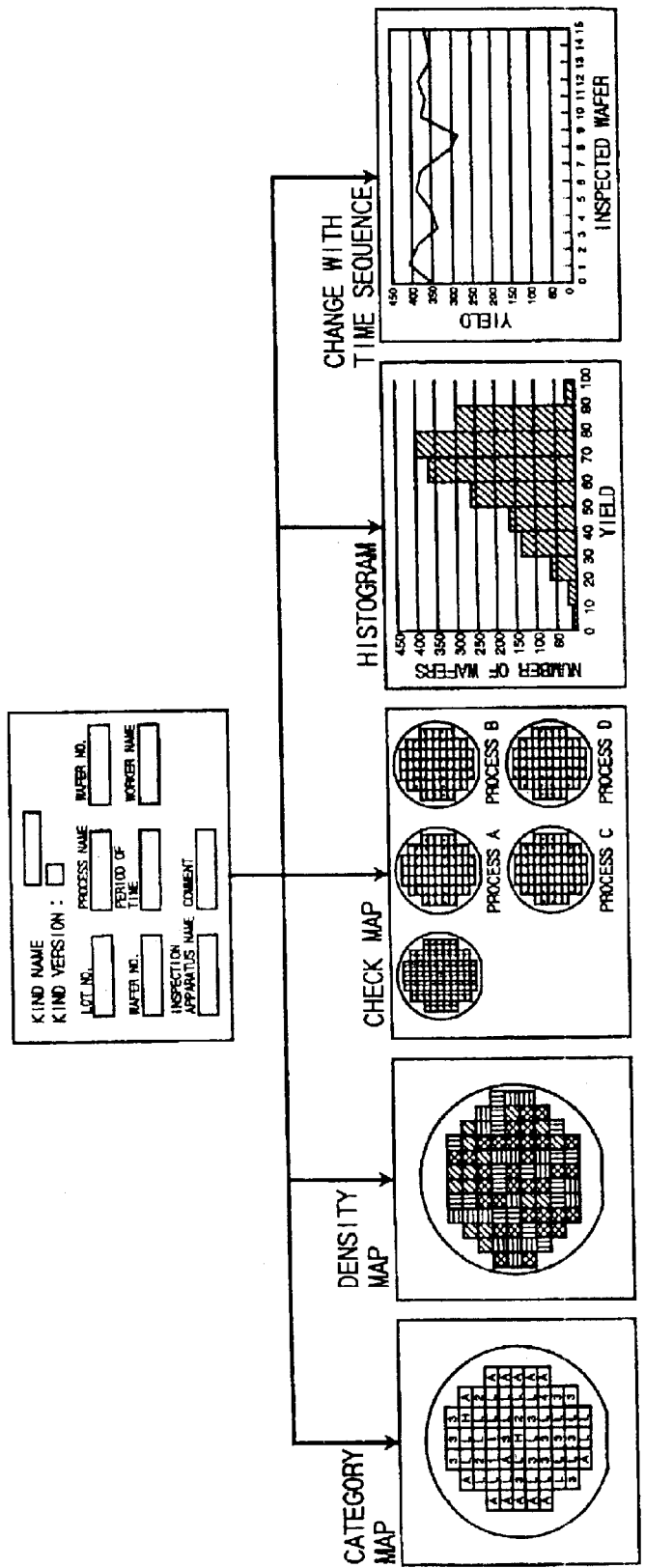
FIG. 8 is a block diagram showing an example of displays of analysis data in a yield analysis.

(2) Yield Analysis Data:

FIG. 8 shows an example of an analysis data display in a yield analysis.

The yield analysis data is obtained mainly based on conforming or nonconforming results of chips obtained from an operating testing apparatus of a semiconductor manufacturing line. The principle will be described below taking the semiconductor manufacturing line connected to the inspection and testing apparatuses and a pattern forming apparatus group as shown in FIG. 1.

An operating test result obtained by the operating testing apparatus of FIG. 1 is registered in the operating test data base 1$b$ as operating test data. At that time, data on the wafer-by-wafer basis of the wafer performed the operating test is registered in the inspection test data base 1$a$ as attached information. At forming yield analysis data, when the operating test data is read out from the data base 1$b$, the attached information is read out together.

Positional coordinate data included in the operating test data is registered with physical positional coordinate data converted from logical positional coordinate data. A positional coordinate converting interface for performing such conversion is provided between the operating test data base 1$b$ and the operating testing apparatus group. The construction of the interface will be described below.

Figure 2:
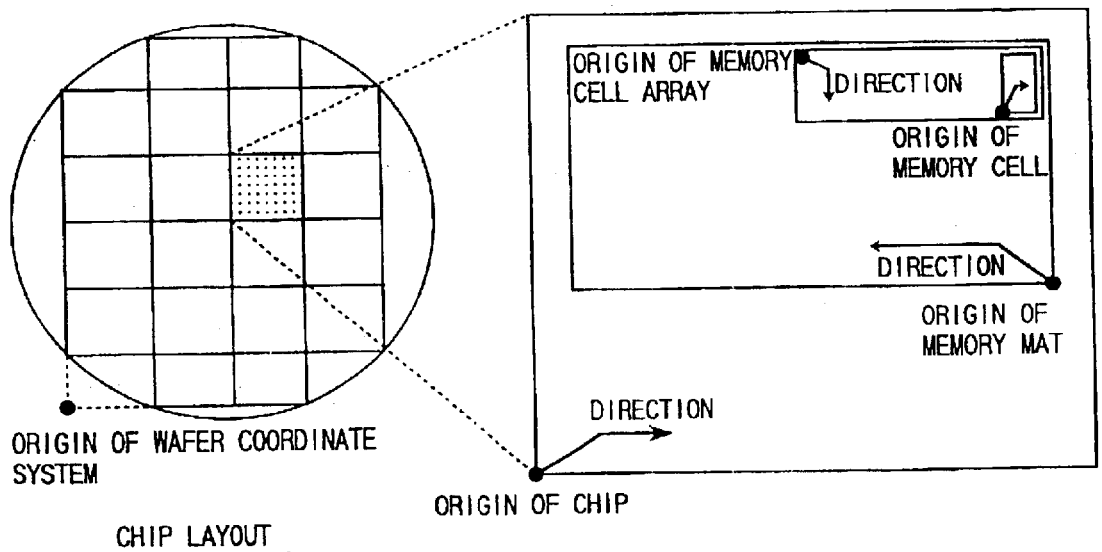
FIG. 2 is a view showing the conversion principle of a logical positional coordinates—a physical positional coordinates of a memory LSI.

FIG. 2 is a view showing the principle of converting logical positional coordinates—physical positional coordinates of a memory LSI. The conversion is performed by a logical positional coordinates—physical positional coordinates conversion table constructed based on the conversion principle shown in FIG. 2. This conversion table has the following construction.

The conversion table comprises 1. a table for positional coordinates and direction of a memory mat in a chip, 2. a table for positional coordinates and direction of a memory cell array on the memory mat and 3. a table for positional coordinates and direction of a memory cell on the memory cell array.

The table No. 1 is a table showing the relationship between the logical coordinate information (pin number and path number used in a test by the operating testing apparatus) and physical coordinate information (memory mat name and the positional coordinates and direction), and is formed in a table as shown in FIG. 3A. The table No. 2 is a table showing the relationship between the logical coordinate information (path number) on the memory mat and physical coordinate information (memory cell array name and the positional coordinates and direction), and is formed in a table as shown in FIG. 3B. The table No. 3 is a table showing the relationship between the logical coordinate information (Y-address and X-address of a testing apparatus) on the memory cell array and physical coordinate information (positional coordinates of the memory cell), and is formed in a table as shown in FIG. 3C.

Figure 4:
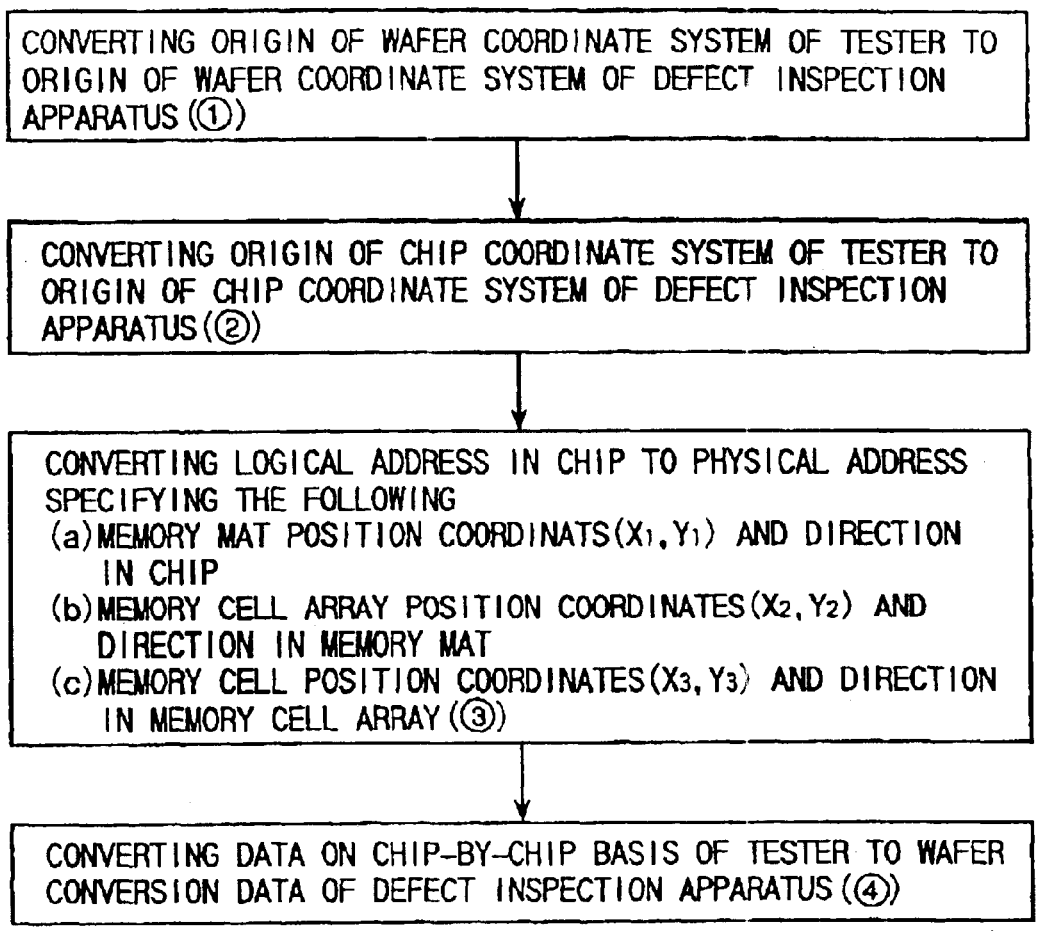
FIG. 4 is a flowchart showing a conversion procedure of a logical positional coordinates—a physical positional coordinates.

In this embodiment, conversion is performed from the logical positional coordinates to the physical positional coordinates using the conversion tables having the structures described above in a procedure shown in FIG. 4.

By having such a construction, it becomes easy to specify a defect which causes fault. That is, since a position of a defect and a position of operating fault can be checked, it becomes easy to specify which defect is a cause of the fault.

Based on the construction, the yield analysis described below becomes possible in the present embodiment.

Initially, conforming probability of a chip on a wafer can be displayed based on the operating test result. This is a means used on an occasion, for example, that the conforming probability of a wafer is calculated on the chip basis, and calculated based the following calculation equation.

(conforming probability of chip)=(number of chips which have been conforming)/(number of tested chips).

This calculation is performed by the analysis station 3*a* or 3*b*. The analysis station comprises a computer for performing the calculation, and the conforming probability can be obtained by reading out conforming item/nonconforming item data of chips from the operating test data base and by dividing number of the conforming items with the total number of the conforming items and the nonconforming items.

Further, it is possible to display the analysis information in the display form of a wafer map shape as shown in FIG. 7.

The display of the first frame in the left hand side of FIG. 8 is a category map. This map displays kinds of operating faults on the chip-by-chip basis. In order to display this kind of display, in the analysis station, kinds of faults to chip positions are specified by reading out the chip coordinate data attaching to the fault classification code data. Further, in the display shown by the center frame in FIG. 8, the category map and the wafer outer appearance are displayed in parallel so that what kind of defect in what process causes what kind of fault can be specified.

As described above, in the present invention, the display described above can be performed by selectively reading out necessary information from the data base or the image file based on an operator's instruction.

Similar to the description in the item of defect map, the yield analysis data can be displayed based on the following specifying condition.

1. Display on the kind basis.
2. Display on the category basis.
3. Checking display.
4. Enlarged display.
5. Image display.
6. Extracting display Further, in the item 1 of display on the kind basis, there are displays on the wafer basis, on the process basis and on the fault basis each of which is specified from the analysis station. In regard to the display on the wafer basis, one of the items consisting of all wafers, the same lot wafers, specified wafers is specified. In regard to the display on the process basis, one of the items consisting of all operating test processes and specified operating test processes is specified. Further, in regard to the display on the fault basis, one of the items consisting of all faults, DC faults and function faults is selected. The display on the fault basis is a special item for the yield analysis data, and by selecting the kind an arbitrary code is selected from kinds of faults registered in the data base.

The item 2 of display on the category basis is an item for selecting and displaying fault data belonging to a fault classification code specified.

The item 3 of checking display is an item for overlapping and displaying, for example, the defect inspection data and the operating test data or two kinds of the operating test data. For example, the display shown by the central frame of FIG. 8 (parallel display of the operating test data and the defect inspection data) is performed by this specification. However, in order to obtain this display, additional specification is required for reading out image files of inspection processes A to D. Kinds of checking conditions will be described below.

In a case of displaying on the wafer basis, a kind of operating test data to be overlapped and displayed is selected from the items consisting of conforming item/nonconforming item, DC fault, function fault, fault classification code and conforming probability of chip. In a case of displaying on the chip basis, a fault position is specified.

Defect inspection data to be overlapped with operating test data is selected based on the following classification items.

Kind of defect

Kind on the process-by-process basis

Kind on the defect-by-defect basis

Objective defect size/measured value

Range

Kind of display

The kinds of defect are wafer surface having an extraneous substance particle attached, pattern defect, patter dimension, pattern overlapping accuracy, film thickness of formed film, in-film stress of formed film, dopant concentration, reticle having an extraneous substance particle attached, reticle defect correction mark, wiring correction mark and so on. The kind on the process-by-process basis is a selective item of all processes or specified process basis. The kind on defect-by-defect basis is a selective item of all defects, fatal defects, non-fatal defects or defects on the classification code basis. The objective defect size or measured value is a selective item for selecting one from specifying all defects or numerically specifying such as specification of a measured value, an upper limit value, a lower limit value or the like. The kind of display is an item for specifying presence or absence of display of the scribe line or specifying presence or absence of display on the area-by-area basis.

Further, the objective wafer is specified by one of all wafers, the same lot wafers and the same wafer.

Furthermore, check condition and the method are specified. The check condition is an item for specifying an allowable range at comparing the coordinate data., and the checking method is an item for selecting how checking the above-mentioned items by selecting out of OR, AND, XOR.

The data based on these selected items is read out from the data base 1 or the image file 2, and displayed on the analysis station 3a or 3b in a predetermined display form.

The item 4 of enlarged display is an item for enlarging and displaying a specified area on a wafer map. The following effective enlarged display can be considered.

Fault position data is enlarged and displayed on the exposing field basis based on the exposing field arrangement data registered in the data base. By performing such a display, defects caused by an apparatus such as a step-and-repeat equipment can be specified.

Further, the fault position data can also be enlarged and displayed on the block basis by dividing the chip arrangement into inspection block units of the inspection apparatus.

Furthermore, the fault position data in a specified area can also be enlarged and displayed.

The item 5 of image display is a function for displaying an image of a reviewed fault position by specifying the fault position.

The item 6 of extracting display is an item for map displaying the yield data in a specified classification interval or in a specified time.

The yield level management display will be described below. The yield level management display is different from the defect level management display described in the item of defect analysis data, and the yield is set to classification interval number in the yield level management display.

In detail, a chart is displayed by taking yield or chip conforming probability as the classification interval number in the abscissa, and by taking number of wafers of which the yield or chip conforming probability is within the classification interval number in the ordinate.

In another example, a chart may be displayed by taking period, wafer or lot in the abscissa and taking yield or chip conforming probability in the ordinate.

Further, a chart is displayed by taking operating test process in the abscissa and taking yield/chip conforming probability in the ordinate. Process tracing can be displayed by this.

The defect inspection data can be displayed as data of change with process based on the following specifying conditions though the similar description has been made in the items of defect map and the display of defect change with process.

1. Display on the kind-by-kind basis
2. Display on the category-by-category
3. Management reference value display A management reference value and statistical processed values such as an average and a deviation are displayed.

Further, in regard to displaying method, graph display or numerical display is selected. Setting of a management reference value is performed by the following two.

Values stored in the data base as inspection data are displayed.

Statistical processing calculated values of storing condition data are automatically set and displayed.

In addition to these, the following conditions are specified at that time.

A processing range is specified any one out of a period before the time point of calculation, cumulated processed lots and number of cumulated processed wafers. The displayed value is selected any one out of average value and average value/deviation. The automatically set management reference value is automatically unloaded to a related inspection apparatus by specification.

In the embodiment of the present invention, when the input inspection data exceeds the management reference value or a fluctuation state deviates from a specified reference, an alarm is set so as to automatically sound.

The specified reference is selectively specified any one of the following.

1. A specified Cp/Cpk value is specified as a reference.
2. In a case of occurrence of a special distribution, alarm is sounded when the state exceeds a certain level.
3. When a defect occurrence frequency of a specified chip is high, alarm is sounded.
4. When a defect occurrence frequency of a specified position of chips is high, alarm is sounded.
5. When a defect occurrence frequency exceeds an allowable defect occurrence frequency, alarm is sounded.

According to this embodiment, a defect chart or a map in a specially specified classified interval or specified time can be displayed.

Further, a report on a specified item is issued with a predetermined time interval and a predetermined format.

(3) Wafer Outer Appearance—Yield Correlation Analysis Data:

In this embodiment, a construction for estimating a yield of wafers or chips from defects in the wafers or the chips is disclosed. The details will be described below.

The semiconductor manufacturing line comprises a plurality of treating processes and a plurality of inspection processes, and semiconductors are completed through these processes.

In the mid time of processing, a yield at the time when wafers or lots are completed is calculated based on inspection data of process defects having obtained from the inspection processes before the present time and a budgetary yield of the following processes. The calculation result, that is, the estimated yield is used, for example, as follows. When the estimated yield is lower than an initial planned value, the wafer or the lot is taken away from the process line in the middle of the processes and a new wafer or lot is additionally prepared in order to make up the deficient production quantity. The taken-away wafer is used in fault analysis or the like in order to make the cause of fault clear. On the contrary, when the estimated yield is substantially larger than the initial planned value, measures such as reducing number of the following wafers or lots or stopping the manufacturing in order to adjust the production quantity.

Such manufacturing management can reflect to more improve the production efficiency as the accuracy of the yield calculation is higher. However, the yield calculation as described above is mostly depending on a sense of an engineer obtained by his experience, and accordingly it is not what anyone can do.

In order to solve this problem, in the present invention, there are provided a means for respectively classifying defects into combinations of elements characterizing wafer defects and a predetermined yield correlation table which shows a yield of wafers or chips on a wafer to the combination of the defect elements.

Figure 9:
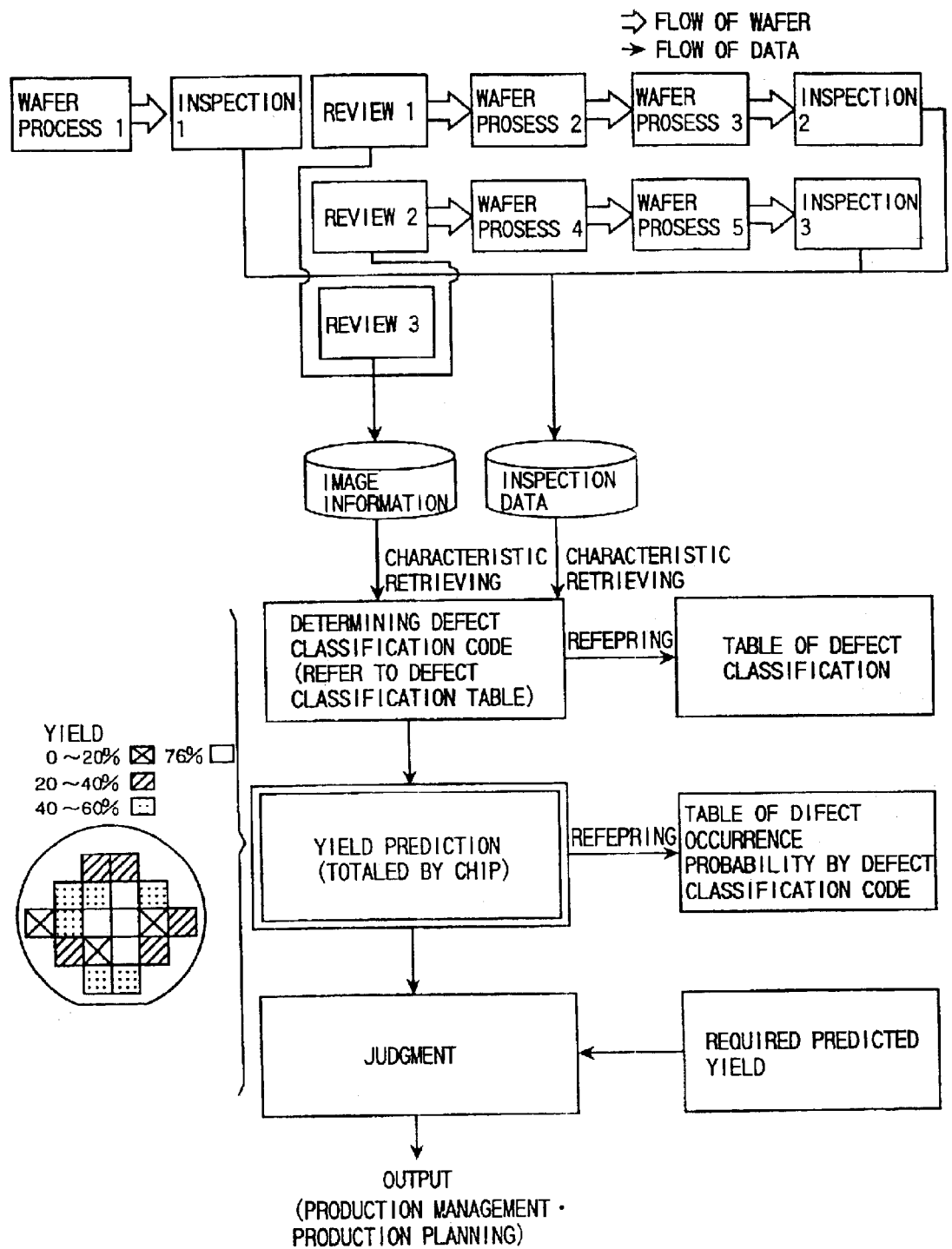
FIG. 9 is a block diagram showing a flow of data in a semiconductor manufacturing line.

The above will be described in detail below, referring to FIG. 9. FIG. 9 is a block diagram showing a flow of data in a semiconductor manufacturing line. Here, the review is a process for reconfirming whether or not the inspection results obtained in the inspection processes are proper, or a process for checking defects recognized by the inspection results in detail. In the embodiment of the present invention, the review is performed based on sample images obtained mainly by a scanning electron microscope for reviewing. The sample image is registered in the image file.

According to this embodiment, defect classification codes are determined according to defect detecting results obtained from the review and the inspection processes. This is the defect classification in the present invention. The defect classification code means a combination of the defect elements described previously. The defect element means an item obtained by fragmenting the defect characteristic item as shown in FIG. 10.

Figure 6:
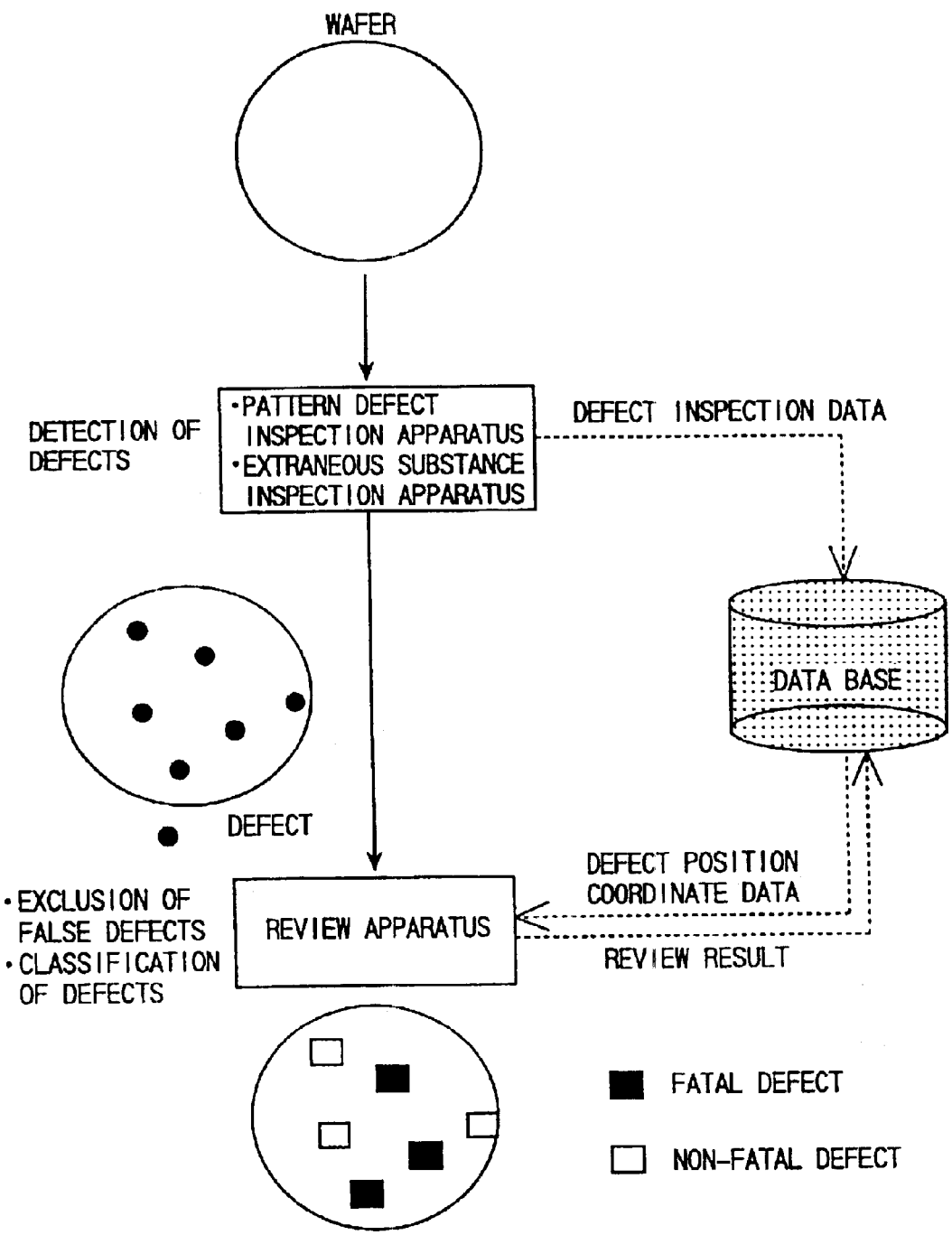
FIG. 6 is a block diagram showing a procedure of detecting and reviewing defects.

The review and the defect detection are practically performed according to the flowchart shown in FIG. 6. A process defect detection result obtained by the pattern defect inspection apparatus or the extraneous substance inspection apparatus on the inspection process is registered in the data base as inspection data based on position coordinate data of a process defect transmitted from the data base, the review apparatus performs positioning of the defect, forming of an image (including judging whether or not the process defect detection result is false information), classification of the defect from the image and transferring the result to the data base.

Then, the defect classification code is registered in the data base as a classification code for the defect.

Methods of determining characteristics obtained from the image information considered are the following two.

1. Classifying by an operator through observing a defect image.
2. Automatically classifying by a computer.

In the above item 1, the defect image and the classification code—characteristic item corresponding table shown in FIG. 10 are displayed on the display unit of, for example, the analysis station or the review apparatus of FIG. 1, and the operator fills out items of the corresponding table while observing the defect image. When the input is completed, characteristic obtained from the image information of the defect image is determined by comparing with classification code to each of the combinations of characteristic items pre-registered. In this case, a model defect image may be installed in the defect classification table.

In the above item 2, a model defect image corresponding to each of the classification codes (a plurality of model defect images may correspond to one classification code) is pre-stored in, for example, the inspection data base/the image file, and a defect image is compared with the model defect images. If there is a model defect image judged to be similar, the defect is classified to the classification code. If a neuro-computer or a fuzzy computer is used for the computer used in the classification, a learning function to improve accuracy of classification can be given to the computer by checking the input model defect and the validity of the classification result and by making the computer learn the correct result.

Practically, a defect classification table is formed using characteristic items extracted from the image information such as shape of defect, size, color, composition, structure and the like and characteristic items extracted from the inspection information such as defect producing process, defect distribution on wafer surface, defect occurrence position and the like, and defect classification is performed by checking an extracted characteristic of the detected defect with the defect classification table.

Particularly, by classifying defect shapes not into geometrical characteristics but into types based on short circuit, line break, projection, chipping-off, pin hole, isolation, the fatal defect can be appropriately classified.

The size is classified not by absolute dimension, but characterized by dividing into degrees, for example, in a case of projecting defect, dividing into below $1/3$ of wiring space, $1/3$ to $2/3$ and above $2/3$. By characterizing the defect shape and the defect size by the above-mentioned elements and the degree instead of the geometrical characteristics and the absolute dimension, classification having a strong correlation with the yield can be realized. In other words, the key point of accurate prediction is to employ a defect classification method having a high validity, that is, to perform classification having a high yield correlation.

The fatal defect means a defect inducing an operating fault of an LSI. By dealing with the analysis information by unifying with the image information as described above, it makes easy to construct a data base and to perform design work of data analysis software. Further, by connecting the physical analyzer group to the communication network and collecting analysis information relating to composition of defect portion/chemical bonding state and structure, the defect classification at SEM reviewing can be performed more appropriately.

In a case of this embodiment, the defect classification is performed according to the flowchart of FIG. 11. In a case of FIG. 11, the inspection information registered in the data base is read out together with the defect information obtained by the review apparatus, and the information is checked with the information items as shown in FIG. 10, and classification codes agreeing with these conditions are given as defect classification codes of the defects.

Since the defect classification codes determined as described above respectively have pre-registered yield predicted values (a table of fault occurrence probability on the defect classification code basis), yield predicted values based on the defects are determined based on the pre-registered yield predicted values.

The predicted values are grouped on the chip basis and calculated as predicted yield values.

Figure 14:
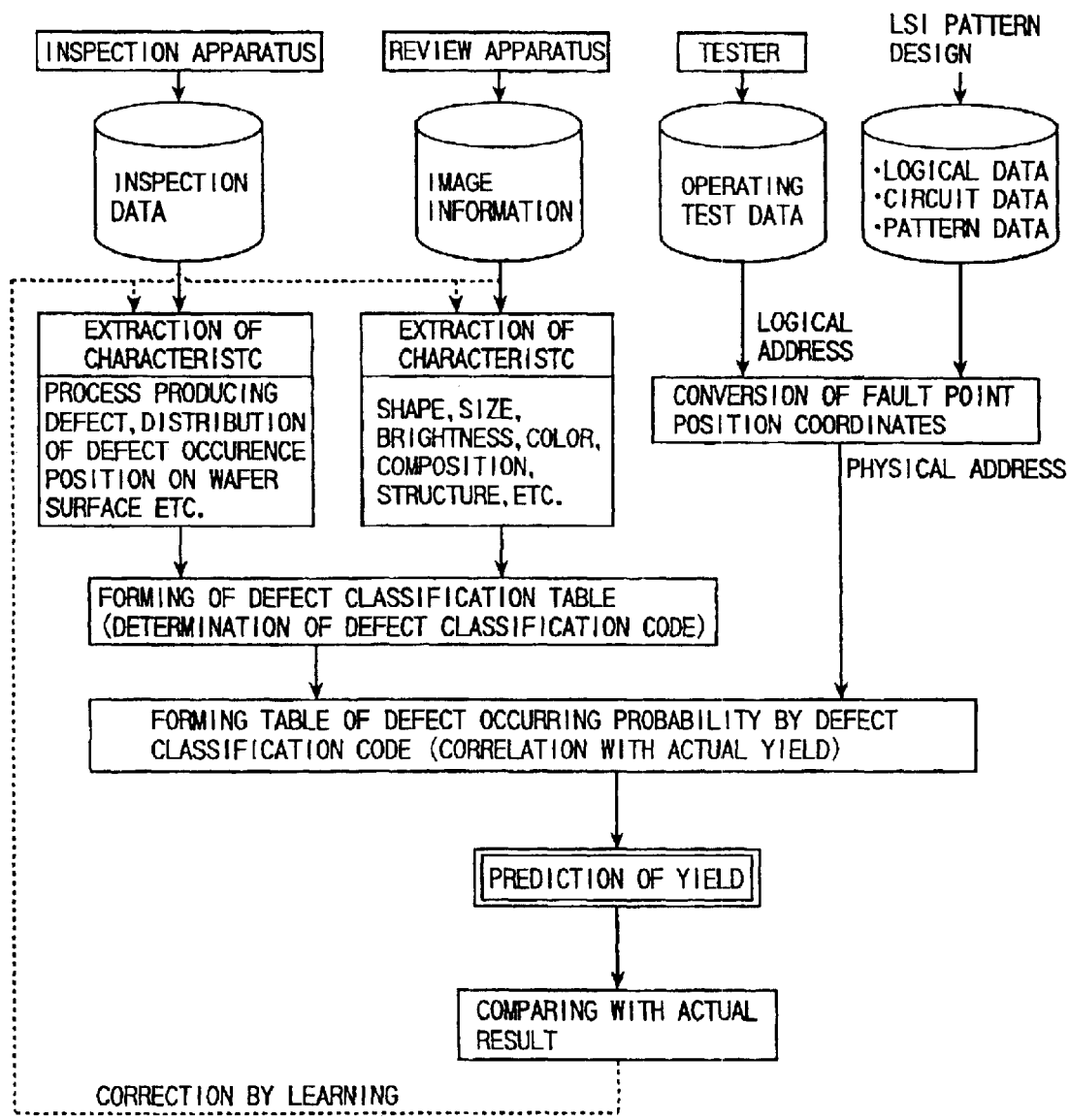
FIG. 14 is a block diagram showing a procedure forming a correlation table of defect classification code—yield value.

In this embodiment, it is necessary to form a defect classification code—yield value correlation table in advance in order to predict yields. The procedure will be described below, referring to FIG. 14.

Initially, a causal relationship between a defect and a fault caused by the defect is obtained in advance, and a yield needs to be confirmed using the relationship. Therefore, it is necessary to know the operating test result obtained from the operating testing apparatus and the defect causing the operating test result. However, there is a problem in that since the operating testing apparatus is operated by logical address, positional relationship between the both is unclear and accordingly the defect causing the fault is difficult to be specified.

Therefore, according to the present embodiment, the problem is solved by separately registering the inspection data collected by the apparatus operated by logical address and the inspection data collected by the inspection apparatus and the testing apparatus operated by physical address (by dividing the data base into two), and by arranging the logical positional coordinate—physical positional coordinate conversion table described in the item of yield analysis data between the both data bases.

Similar to the work at reviewing described above, in this embodiment, a defect classification table (defect classification code) is formed based on characteristics obtained from the inspection data obtained in the inspection apparatus and characteristics obtained from the image information obtained in the review apparatus. Then, the table of fault occurrence probability on the defect classification code basis is formed by checking the operating test result having the physical positional coordinate data using the logical positional coordinate—physical positional coordinate conversion table described above.

This probability table is used for the yield prediction as described previously. Each of the characteristic items is corrected by comparing with the actual result, which is to be described later.

In this embodiment, the defect size calculation equation can be defined by specifying a defect size or measured value condition described above in the item of yield analysis data when a wafer having extraneous substance particles attached or a size of pattern defect (defect size) is determined.

This is because a probability to cause a fault is different depending on a pattern concerned even if the defects are similar to each other. For example, a defect having a long length in x-direction has a probability to cause a fault higher to a line-and-space pattern in y-direction than to a line-and-space pattern in x-direction. That is, even if the defects are similar to each other, the defect classification should be performed so as to meet the object to be analyzed. In this embodiment, in taking such a condition into consideration, classification most suitable to the yield prediction can be performed on defect size by defining the defect size calculation equations.

Further, in this embodiment, a data area in a chip used fir analysis at data analyzing can be specified, For example, an area may be divided into a high pattern density area and a low density pattern area, or a memory cell area and a peripheral circuit area of a memory LSI, or a gate area and a wiring area of a gate array.

As for the pattern density, that is, an isolation degree, data formed at pattern forming can be diverted. For example, in a case where a pattern is formed using an electron beam patterning apparatus, a quantity of exposure is determined depending on a pattern density in order to reduce deterioration in the fidelity of pattern due to the proximity effect. It can be considered that the pattern forming apparatus such as an electron beam patterning apparatus is online connected to the system, and pattern density data obtained from the pattern forming apparatus is used for data analysis.

Figure 12:
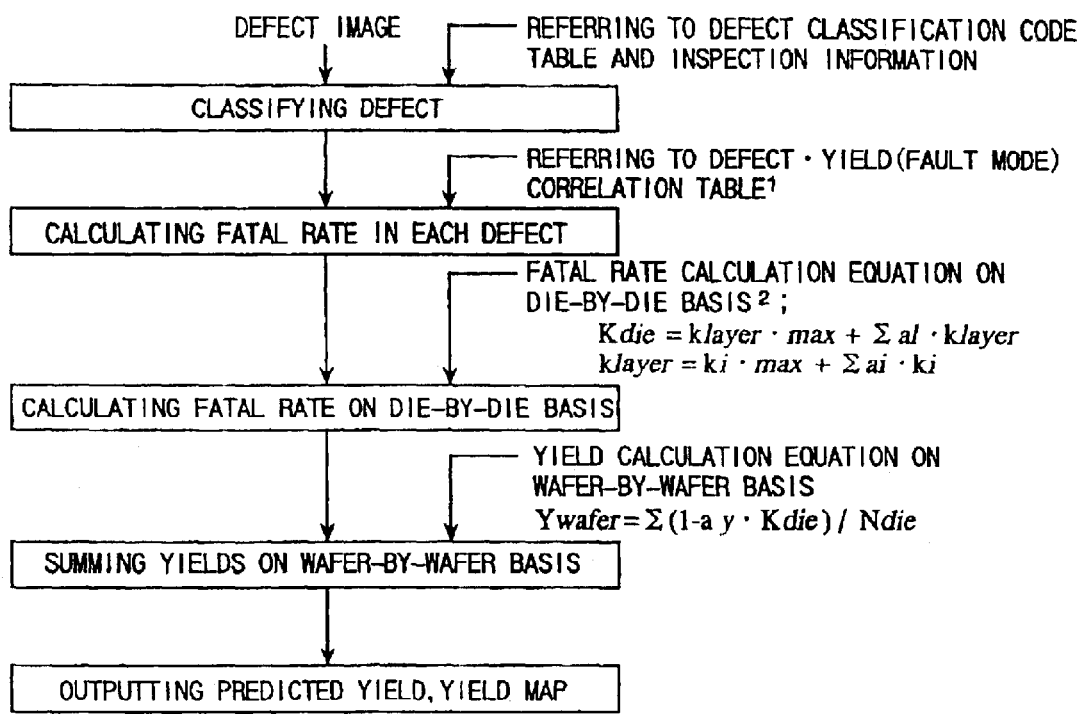
FIG. 12 is a flowchart showing a procedure for outputting a yield predicting value.

The yield predicting value obtained in such a manner is grouped on the chip bases as shown in FIG. 12 and finally grouped on the wafer basis to form a wafer map as shown in FIG. 12.

The defect classification codes in this embodiment are corrected by comparing with the actual result, as described previously. The accuracy of defect classification (the defect classification table and the model defect) means a strength of correlation between classification and fault. That is, it can be said that the more accurate the defect classification is, the stronger the correlation between the classification and the fault is. Having a stronger correlation means having capability of predicting a more accurate yield. In the present invention, in order to obtain a strong correlation, the inspection information such as defect producing process and the defect fault analysis information such as composition of a defect portion are used in addition to the characteristic extraction from the review image information such as defect shape when defects are classified. Further, in order to obtain a stronger correlation, the defect classification codes are continuously optimized.

The optimization is performed, for example, using a method to be described later by checking the defect classification or the yield prediction result with a yield of chip having defects or an actual result of fault. The items, contents and model defects in the defect classification table are reviewed any time so as to attain a better correlation.

It is preferable to provide a function which is capable of adding on the chip basis and displaying defects re-counted setting net defects (defects produced in the present process) and/or clustering defects to a pre-determined number (0, 1, . . . , number of chips covered by the clustering) using the defect classification code as a key when the defect classification codes are determined and the validity (correspondency with fault mode) is checked. In a case of the present embodiment, number in each of the defect classification codes registered in the data base is added on the chip basis or on the specified area basis by the analysis station which has a function to execute the above calculation.

The reason why the net defects and the clustering defects are counted in a manner as described above is based on an empirical knowledge that "good correlation with a yield can be attained by performing such a counting".

Figure 13A:
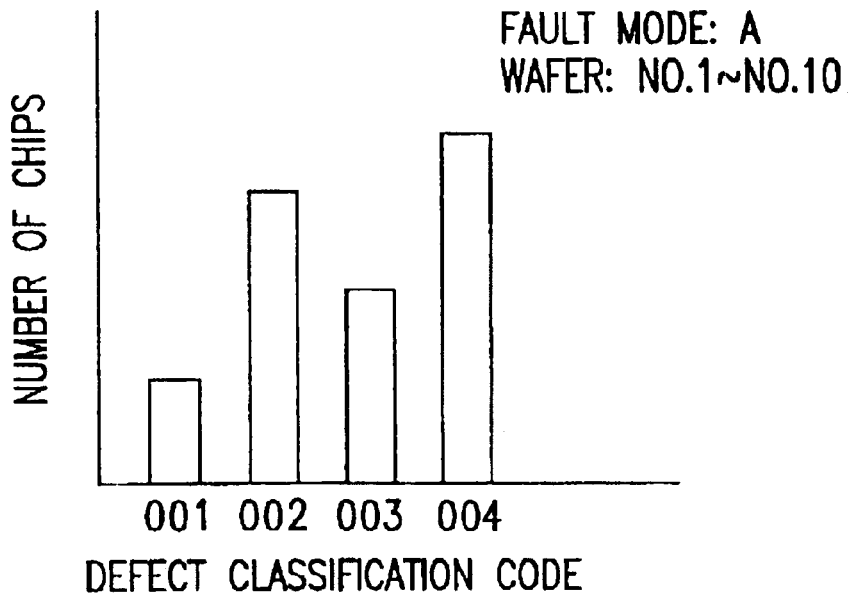
FIG. 13A is graph showing a correlation between defect classification code and number of chips.

For example, FIG. 13A shows an example in which defect classification code is taken in the abscissa and number of chips having the defect or fault ratio is taken in the ordinate for wafers within a predetermined retrieving range in taking fault mode as a parameter. This embodiment also has a function to perform such a display.

In FIG. 13A, if a specified defect classification code has a strong correlation with the fault ratio, it indicates that the defect classification is appropriate in that degree. If any defect code has no strong correlation with the fault ratio, it indicates that the defect classification is inappropriate. If faults are classified so as to have a strong correlation with a specified defect code, a cause of producing defects can be easily detected and accordingly the yield can be improved in a short time, and the yield can be accurately predicted.

In this embodiment, the correlation between defect code and fault can be made stronger by re-setting the defect classification codes.

Therefore, classification codes not existing before are newly set and a function to register them is provided. This function is that the operator fills out each of the characteristic items as shown in FIG. 10 at the analysis station, and new defect classification codes are formed by adding new classification codes to combinations of the new characteristic items (elements). The newly formed defect classification codes are registered in the data base.

If new defect classification codes are set and a stronger correlation can be obtained by the new classification codes, the classification is performed more appropriately. A state obtained by the strong correlation here means a state that in FIG. 13A, number of defects having a specified classification code is extremely increased compared to number of defects having another classification code.

In a case of an LSI having a rescue function such as a D-RAM product, it is possible to use a fault chip rescue ratio instead of the fault ratio. By doing so, the yield improving effect by rescue can be introduced in the yield prediction. The rescue is performed in such a manner that a wire of a failed circuit is cut using a laser for working and connected to a redundant circuit for rescue. Therein, the fault or fault chip rescue ratio sometimes depends on number of defects in the chip. In such a case, number of net defects in a chip described above is displayed in addition to the fault mode.

Further, in order to roughly perform a yield prediction, it is preferable to provide a function capable of adding and displaying defects re-counted by setting number of net defects and/or clustering defects to a predetermined number on the wafer basis as a key of an average number of defects per wafer or a defect density.

Figure 13B:
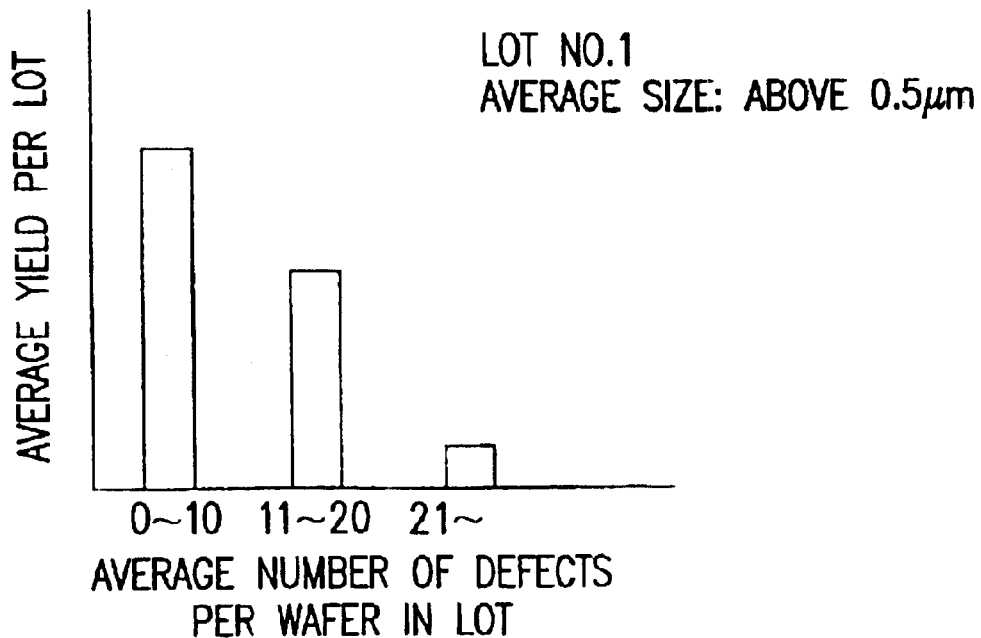
FIG. 13B is a graph showing a correlation between lot within a preset range and average value per chip or wafer.

For example, FIG. 13B shows an example in which average number of defects per wafer or chip is taken in the abscissa and average yield per lot is taken in the ordinate for wafers within a predetermined range in taking defect size as a parameter. By seeing the figure, from data on number of defects in an inspected wafer concerned, a yield of the wafer can be easily estimated. Fault ratio may be taken in the ordinate instead of average yield. Failed chip rescue ratio may be also taken in the ordinate.

In calculating the average value, it is not always necessary to average values over all the wafers in a lot. One wafer having the data may represent an average value.

Further, the present invention provide the following function for yield prediction.

Based on the result of checking between defect inspection data and operating test data, a fatal ratio of each chip is calculated to predict a yield of a wafer. In the prediction, the defect map on the basis of defect classification code and defect classification code—yield scatter diagram are used.

The predicted results of a yield value and a fault ratio are displayed in the forms of map and chart.

The wafer outer appearance—yield analysis data displays defect—defect correlation or defect—yield correlation based on the defect inspection data and the operating test data. The wafer outer appearance—yield correlation analysis is composed of functions of scatter diagram and correlation coefficient diagram in addition to data base retrieving.

a. Scatter Diagram:

A scatter diagram displays correlation between defect and yield. The following are displayed.

(a-1) Defect—defect scatter diagram: Scatter diagram is displayed by taking number of defects/size of defect or measured value/defect classification code in the abscissa, and by taking number of defects/size of defect or measured value/defect density or defect probability/defect fault ratio in the ordinate. The same item may be taken in both of the ordinate and the abscissa.

(a-2) Defect—yield scatter diagram: Scatter diagram is displayed by taking number of defects/size of defect or measured value/defect density or defect probability/defect fault ratio or defect classification code in the abscissa, and by taking yield in the ordinate.

The scatter diagram has the following sub-menu.

1. Classification Display

Data is displayed by selecting the data from the following and using AND condition when a plurality of items are specified.

Wafer classification: ① all wafers, ② wafers in the same lot, ③ classification on the specified wafer basis.

Operating test process classification: ① all operating test processes, ② classification on the specified operating test process basis.

Fault classification: ① all faults, ② DC faults, ③ function faults, ④ fault classification code basis.

Inspection process classification: ① all processes, ② classification on the specified process basis, ③ a process at present time, ④ processes before the process at present time.

Defect classification: ① all defects, ② fatal defects, ③ non-fatal defects, ④ defect classification code basis.

Defect size/measured value: ① all defects or all measured values, ② upper limit, ③ lower limit, ④ range.

Inspection data range: presence/absence of area specification.

2. Management Reference Value Display:

A management reference value and statistical processed values such as average value and deviation are displayed.

Display method, management reference value setting method and alarm method are selected from the following.

Display method: ① graph display, ② numerical display.

Management reference value setting method:

Values stored in the data base as inspection condition data are displayed. Statistical processed values of the stored operating test data are calculated, and automatically set and displayed.

At that time, the following are specified.

Processing range: ① period before the calculation time point, ② number of cumulative processed lots, ③ number of cumulative processed wafers.

Display value: ① average value, ② average value/deviation.

The automatically set management reference value may be automatically unloaded to the related operating testing apparatus on specification.

Alarm method: Alarm is automatically sounded when input operating test data exceeds a management reference value or a fluctuating state is deviated from a specified reference.

The specified reference is specified from the following under OR condition.

① Cp/Cpk value by specifying, ② occurrence of special distribution, ③ high frequency of occurrence of fault in a specified chip, ④ high frequency of occurrence of fault in a specified position in a chip, ⑤ allowable frequency of occurrence of fault.

Yield data of a specified classification interval or a specified period is displayed in the form of a chart or a map.

3. Basic Statistical Value Display:

Correlation coefficients are displayed on specification.

4. Regression Straight Line Display:

A regression straight line by minimum-square method is displayed on specification.

5. Automatic Reporting:

A report on a specified item is automatically issued with a predetermined time interval and a predetermined format.

(b) Correlation Coefficient Diagram:

Correlation coefficients of defect inspection data—defect inspection data, defect inspection data—yield data are displayed.

The following sub-menus are provided. The contents of the sub-menu follows those of the scatter diagram described above.

1. Classification Display

2. Management reference value display

3. Basic statistical value display

4. Regression straight line display

5. Automatic reporting

Although the examples have been described in connection with semiconductor device manufacturing, the above can be applied to process management of display devices, camera devices and so on in addition to the semiconductor devices.

(4) Download of Commonly Used Data:

The system of the present invention has the following two functions for downloading data commonly used in each of the inspection apparatuses to each of the apparatuses. The outline will be described below.

A first function is executed as follows.

In the inspection apparatus A connected to the communication network of FIG. 1, an operator A inspects wafers by changing an inspection condition based on work instruction. After completion of the inspection, the operator A transmits and registers the changed inspection condition to the data base 1 together with the inspection data. The analysis station 3 notifies pre-designated apparatuses B, C, . . . belonging to the same group as the apparatus A that the inspection condition has been changed. When an operator B starts inspection work at the inspection apparatus B, the notice that the inspection condition has been changed is displayed on the display unit of the analysis station. The operator B reads out the new inspection condition from the data base and updates the inspection condition of the inspection apparatus B. Then, the operator B inspects wafers under the new inspection condition.

This function is that the analysis station notifies pre-designated apparatus group that the inspection condition has been changed. The inspection apparatus connected to the communication network has a means for displaying the notice.

A second function is executed as follows.

In the inspection apparatus A, an operator A inspects wafers by changing an inspection condition based on work instruction. After completion of the inspection, the operator A transmits and registers the changed inspection condition to the data base together with the inspection data. The analysis station transmits the new inspection condition to pre-designated apparatuses B, C, . . . belonging to the same group as the apparatus A to rewrite the inspection conditions.

By this function, the data base and each of the inspection apparatuses connected to the communication network can rewrite the inspection conditions.

Figure 15:
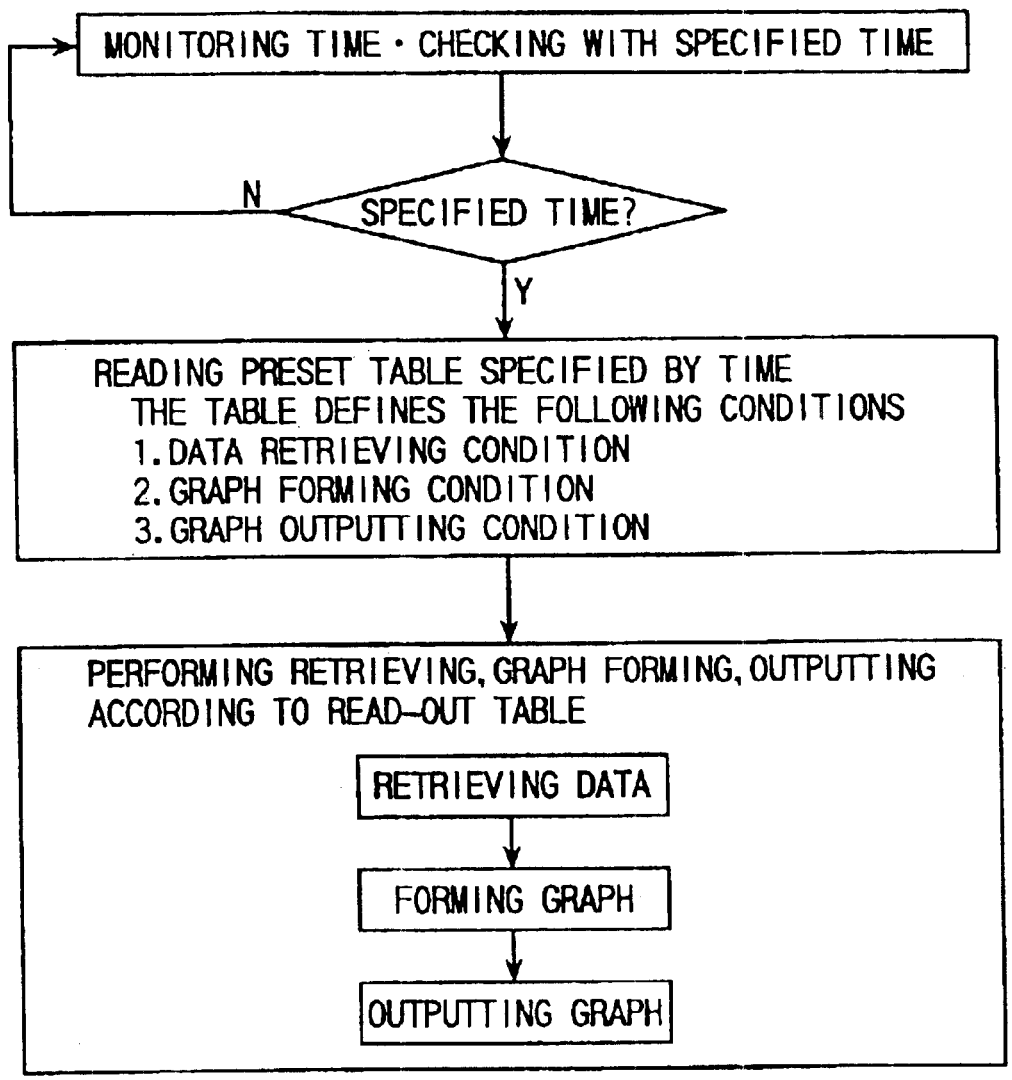
FIG. 15 is a flowchart showing an automatic reporting function in accordance with the present invention.

The semiconductor manufacturing line has a specific characteristic that a plurality of inspection apparatuses of the same kind are connected, and species data and wafer data are commonly used in each of the inspection apparatuses connected to the communication network. By providing the function described above, even if data is corrected or changed in one of the inspection apparatuses, apparatus data in the inspection apparatuses of the same kind is corrected or changed. Therefore, the input work and the probability of input miss can be substantially reduced, (5) Automatic Reporting:

Issue of report described above is performed as follows. The automatic reporting will be described below, referring to FIG. 15.

An operator presets a table determining date to issue a report and data retrieving condition, graph forming condition and graph printing condition for forming the report. The following program is automatically executed based on the setting.

The analysis station reads time by a clock in the system. A preset specified time initiates the following program to be executed.

The table of retrieving condition, graph forming condition and graph printing condition preset by the operator is read out at specified time. Then data is retrieved according to these conditions. Similarly, graph displays or print outputs are output to pre-designated clients according to these conditions.

According to the present invention, by existence of the function described above, it is possible to periodically monitor the semiconductor manufacturing line the state of which is changed every moment.

In order to attain a high yield and stable production in the semiconductor manufacturing line, a level of the manufacturing process needs to be managed highly accurately. However, the highly accurate level management increases number of items to be managed, and accordingly burden to the management is increased. Therefore, it is required to reduce the management burden. The above-mentioned automatic reporting is a function to be a help of reducing the burden.

(6) Setting of Management Reference Value:

The setting of the management reference value described above is performed as follows.

Figure 16:
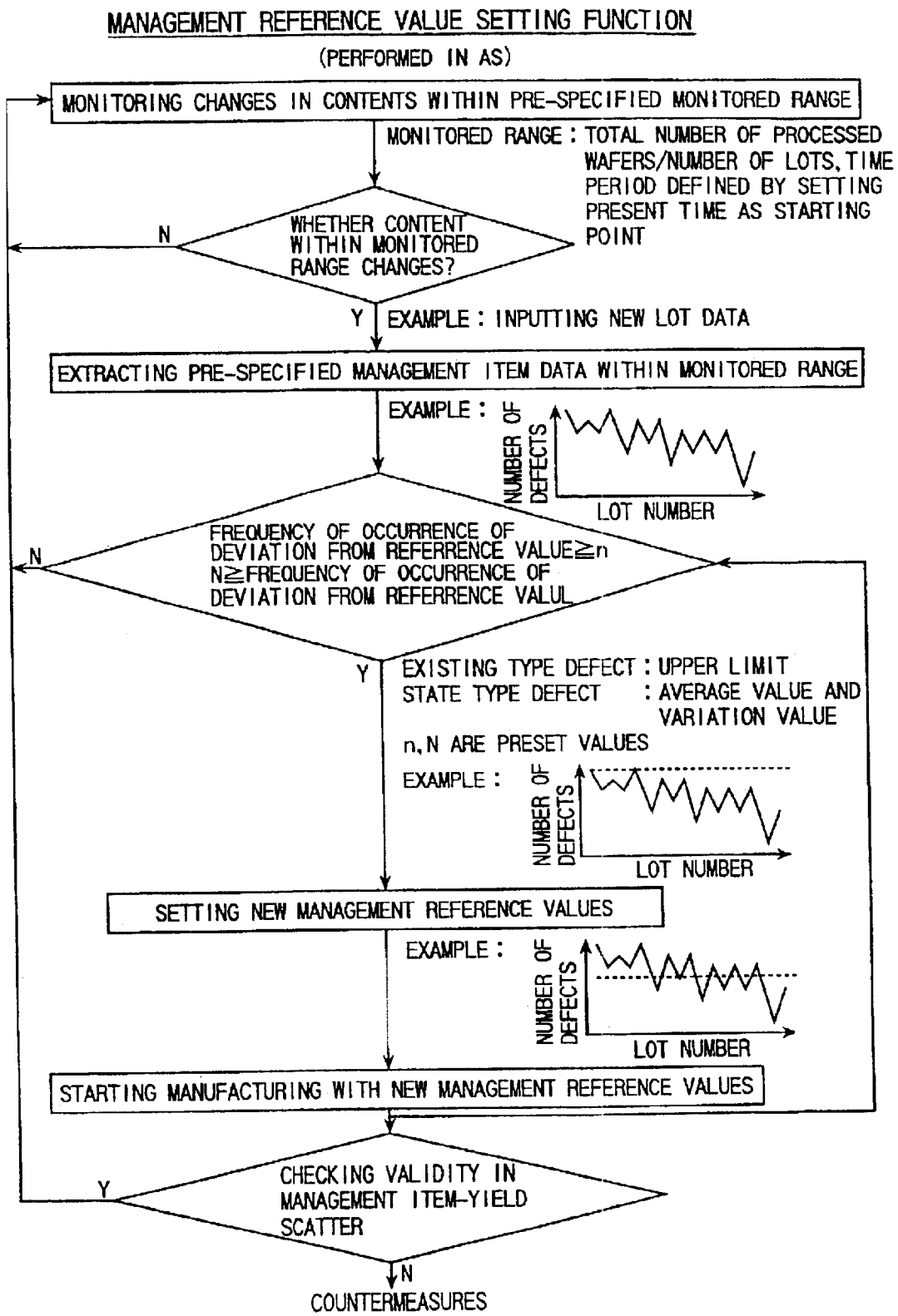
FIG. 16 is a flowchart showing a management reference value setting function in accordance with the present invention.

The setting of the management reference value will be described below, referring to FIG. 16.

An operator presets and registered the following to the data base.

Objective ranges are set according to the degrees of importance. The objective ranges are management items, management reference value monitoring ranges (cumulative number of wafers, cumulative number of lots, period and so on). A scatter diagram between each of the management items and the yield is used to review and select the management items. An allowable frequency of deviation from reference is set for each of the objects. The references are an upper limit for the existing type defects and a deviation for the state type defects. A reference for calculating new reference values is set. The reference is new reference value setting ranges (cumulative number of wafers, cumulative number of lots, period and so on) and a frequencies deviating from reference under the new reference.

Based on the above set values, the change in the contents of the management reference value monitoring ranges initiates the following program to be automatically executed.

Data within the objective ranges is retrieved. The frequency deviating from reference is judged. If the frequency deviating from reference is below a set value, new management reference values are calculated and permission of starting manufacturing under the new management values is asked to the operator. Then the manufacturing under the new management values is started on an operator's instruction to the inquiry.

In order to attain a high yield and stable production in the semiconductor manufacturing line, a level of the manufacturing process needs to be managed highly accurately. However, the highly accurate level management increases number of items to be managed, and accordingly burden to the management is increased. Therefore, it is required to reduce the management burden. The function of setting the management reference values described above is a function to be a help of reducing the burden.

(7) Alarm Sounding:

The alarm sounding function described above is performed as follows.

Figure 17:
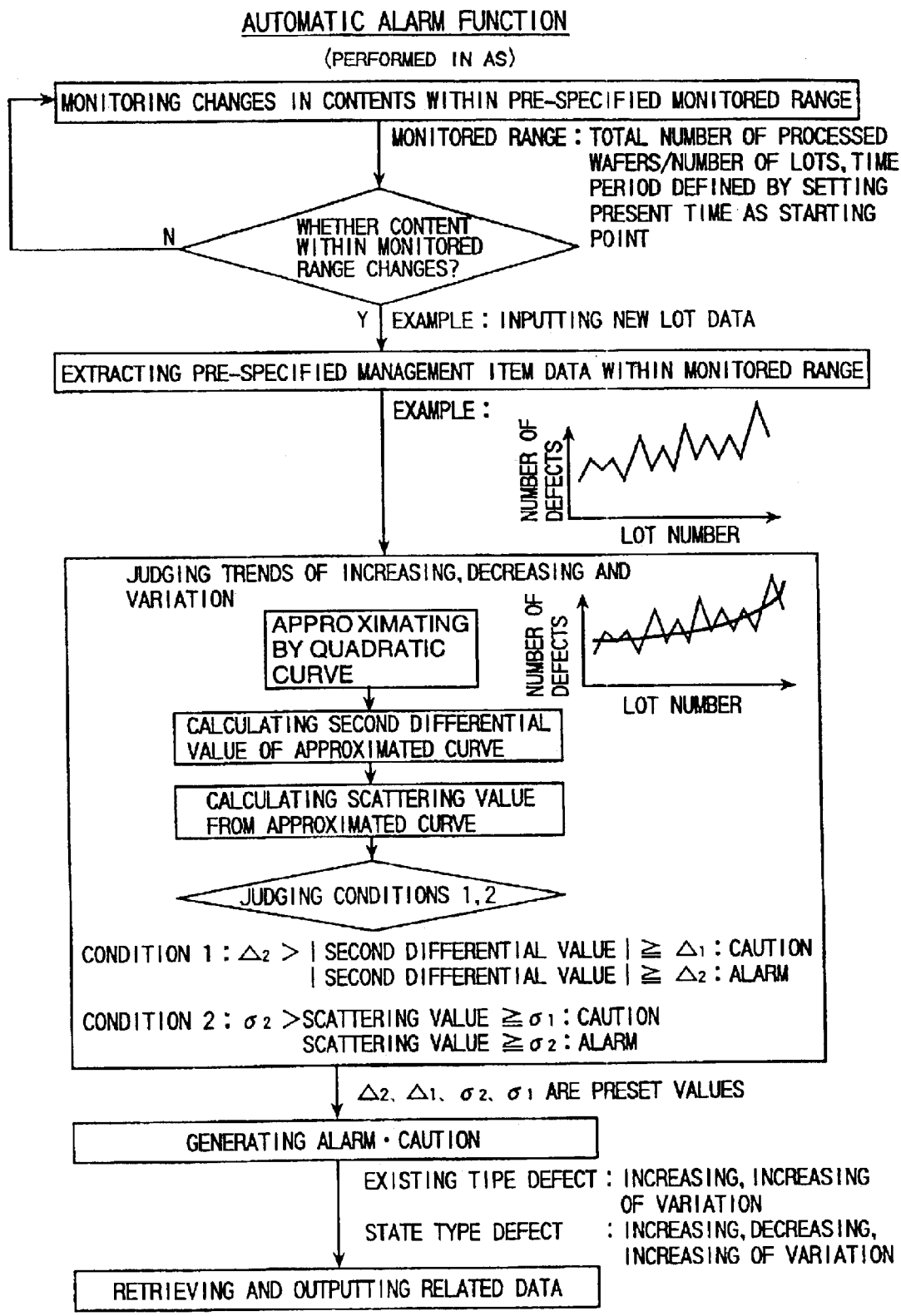
FIG. 17 is a flowchart showing an automatic alarm function in accordance with the present invention.

The alarm sounding will be described below, referring to FIG. 17.

An operator presets and registered the following.

Objective ranges are set according to the degrees of importance. The objective ranges are management items, management reference value monitoring ranges (cumulative number of wafers, cumulative number of lots, period and so on). A scatter diagram between each of the management items and the yield is used to select and review the management items. Next, an alarm and a caution generating reference values are set for each of the objects. The references are an increase and a degree of deviation for the existing type defects, and an increase, a decrease and a deviation for the state type defects.

Based on the above reference values, the change in the contents of the monitoring ranges initiates the following program to be automatically executed. Data within the objective ranges is retrieved, and trends of increase, decrease and deviation are judged according to the following procedure.

Change of data is approximated by a quadratic curve. The second derivative of the approximate curve is calculated.

A deviation is calculated from the approximate curve of the change of data. The second derivative and the deviation are compared with the alarm and the caution generating reference values.

If the second derivative or the deviation is deviated from the alarm or the caution generating reference value, an alarm or a caution is generated and data related to the management item of the alarm or the caution is retrieved and output.

In order to attain a high yield and stable production in the semiconductor manufacturing line, a level of the manufacturing process needs to be managed highly accurately. However, the highly accurate level management increases number of items to be managed, and accordingly burden to the management is increased. Therefore, it is required to reduce the management burden. The function of generating alarm described above is a function to be a help of reducing the burden.

What is claimed is:

1. A process management system including a plurality of inspection apparatuses for inspecting defects, each defect located at a defect location, on a wafer of a chip, said plurality of inspection apparatuses being connected through a communication network, each of said plurality of inspection apparatuses being arranged in manufacturing processes, inspection information and image information which are obtained from said plurality of inspection apparatuses being collected to construct a data base and an image file, said system comprising:

a data base storing results of reviewing defects sent from a defect reviewing apparatus, which reviews defects at locations which are obtained from the inspection apparatus, the results including classifying the defects by combinations of elements characterizing the defects;

comparison means for comparing each defect location with a malfunction location obtained from yield analysis data with reference to the result stored in the data base, the malfunction location being a location at which a defect will result in a malfunction; and display means for displaying results of the comparison.

2. The process management system according to claim 1, further comprising means for calculating a yield of either a wafer having defects or a chip having defects from said combinations of elements characterizing the defects obtained from said defect reviewing apparatus.

3. The process management system according to claim 1, wherein said defect reviewing apparatus uses a selection of a defect by one of said plurality of inspecting apparatuses, connected to said communication network, for selecting an arbitrary defect on the wafer.

4. The process management system according to claim 1, further comprising means for calculating a yield of any one of said wafer or chip having defects from a result obtained from said combinations of elements characterizing the defects obtained from said defect reviewing apparatus, said means for calculating comprising means for setting a yield inspect to said combinations of elements characterizing the defects.

5. The process management system according to claim 1, wherein one of said combinations of elements characterizing the defects is an image characteristic of the defects which is derived based on the inspection information obtained from at least one inspection apparatus of said plurality of inspection apparatuses connected to said communication network and the image information obtained from at least one inspection apparatus of said plurality of inspection apparatuses.

6. The process management system according to claim 1, wherein said defect reviewing apparatus by combinations of elements characterizing the defects obtains elements of said combinations of elements based on said inspection information and said image information.

7. The process management system according to claim 1, wherein said defect reviewing apparatus comprises means for setting a combination of elements characterizing the defects.

8. The process management system according to claim 1, further comprising a computer for adding a number of defects for each of said combinations of elements characterizing the defects.

9. The process management system according to claim 1, further comprising means for displaying each of the elements which said combinations of elements characterizing the defects have.

10. A process management system including a plurality of inspection apparatuses for inspecting defects, each defect located at a defect location, on a wafer, said inspection apparatuses being connected through a communication network, inspection information and image information obtained from said inspection apparatuses being collected to construct a data base and an image file, said system comprising:

selecting means for selecting an equation used for calculation processing from a plurality of pre-stored calculation equations stored in the data base when a size of a defect is specified based on an image using a defect reviewing apparatus obtained from said inspection apparatuses;

comparison means for comparing each defect location and a malfunction location, the malfunction location being a location at which a defect will result in a malfunction, the malfunction location obtained from yield analysis data that indicate the relationship between the size of each defect and the malfunction location, and display means for displaying results of the comparison.

* * * * *